US012582719B2

(12) United States Patent
Shim et al.

(10) Patent No.: US 12,582,719 B2
(45) Date of Patent: Mar. 24, 2026

(54) CHIMERIC COMPOUNDS AND METHODS OF MANAGING NEUROLOGICAL DISORDERS OR CONDITIONS

(71) Applicant: Emory University, Atlanta, GA (US)

(72) Inventors: Hyunsuk Shim, Atlanta, GA (US); Huw Davies, Atlanta, GA (US); Hyun Park, Atlanta, GA (US); Yoon Hyeun Oum, Marietta, GA (US)

(73) Assignee: Emory University, Atlanta, GA (US)

( * ) Notice: Subject to any disclaimer, the term of this patent is extended or adjusted under 35 U.S.C. 154(b) by 803 days.

(21) Appl. No.: 17/433,688

(22) PCT Filed: Feb. 25, 2020

(86) PCT No.: PCT/US2020/019707

§ 371 (c)(1),
(2) Date: Aug. 25, 2021

(87) PCT Pub. No.: WO2020/176513

PCT Pub. Date: Sep. 3, 2020

(65) Prior Publication Data

US 2022/0133892 A1 May 5, 2022

Related U.S. Application Data

(60) Provisional application No. 62/810,009, filed on Feb. 25, 2019.

(51) Int. Cl.
*A61K 47/54* (2017.01)
*A61K 47/55* (2017.01)
*A61P 25/24* (2006.01)

(52) U.S. Cl.
CPC ............ *A61K 47/545* (2017.08); *A61K 47/54* (2017.08); *A61K 47/542* (2017.08); *A61K 47/55* (2017.08); *A61P 25/24* (2018.01)

(58) Field of Classification Search
CPC ................................................ A61K 47/545
See application file for complete search history.

(56) References Cited

U.S. PATENT DOCUMENTS

| | | | | |
|---|---|---|---|---|
| 9,233,161 | B2 | 1/2016 | Kandula | |
| 10,207,984 | B2 * | 2/2019 | Davies | C07C 227/04 |
| 2008/0096889 | A1 | 4/2008 | Minucci | |
| 2010/0022543 | A1 | 1/2010 | Melvin | |
| 2015/0119452 | A1 * | 4/2015 | Kandula | A61K 31/385 549/39 |
| 2016/0244403 | A1 | 8/2016 | Davies | |
| 2018/0016282 | A9 | 1/2018 | Holson | |

FOREIGN PATENT DOCUMENTS

| | | |
|---|---|---|
| WO | 2003053915 | 7/2003 |
| WO | 2012145234 | 10/2012 |
| WO | 2017195216 | 11/2017 |
| WO | 2018178060 | 10/2018 |

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*

"Find ETDs Home » Thesis Resources » Find ETDs" Online: "https://ndltd.org/thesis-resources/find-etds/" Accessed Jan. 31, 2023.*

Irwin "ZINC—A Free Database of Commercially Available Compounds for Virtual Screening" J. Chem. Inf. Model. 2005, 45, 177-182.*

Kim "PubChem in 2021: new data content and improved web interfaces" Nucleic Acids Research, 2021, vol. 49, Database issue Published online Nov. 5, 2020.*

STN Registry/Zregistry (CAS Registrysm) Sep. 2016 2 pages.*

Bonnaud, Journal of Medicinal Chemistry (1987), 30(2), 318-25.*

Venkatesh, J. Pharm. Sci. 89, 145-154 (2000) (p. 146, left column).*

J. G. Cannon, Chapter Nineteen in Burger's Medicinal Chemistry and Drug Discovery, Fifth Edition, vol. I: Principles and Practice, Wiley-Interscience 1995, pp. 783-802, 784.*

Bahia et al. Generation of Selective TACE Inhibitors: Ligand and Structure Based Molecular Modeling, Virtual Screening, Counter Pharmacophore Screening to Get Selective Molecules, QSAR Comb. Sci. 28, 2009, No. 11-12, 1317-1333.

Chepiga et al. Guide to Enantioselective Dirhodium(II)-Catalyzed Cyclopropanation with Aryldiazoacetates, Tetrahedron. 2013, 69(27-28).

Covington et al. Hippocampal-Dependent Antidepressant-Like Activity of Histone Deacetylase Inhibition.

Duan et al. Design and synthesis of tranylcypromine derivatives as novel LSD1/HDACs dual inhibitors for cancer treatment, European Journal of Medicinal Chemistry, 140 (2017) 392-402.

Jochem et al. Antidepressant-Like Properties of Novel HDAC6-Selective Inhibitors with Improved Brain Bioavailability, Neuropsychopharmacology (2014) 39, 389-400.

Kozikowski et al. Searching for Disease Modifiers—PKC Activation and HDAC Inhibition—A Dual Drug Approach to Alzheimer's Disease that Reduces AB Production while Blocking Oxidative Stress, ChemMedChem. 2009, 4(7): 1095-1105.

Pydimarry et al. Rapid Quantitative Determination of Related Substances and Degradants in Milnacipran, Journal of Chromatographic Science 2014, 52:42-51.

Wang et al. Rhodium-catalyzed enantioselective cyclopropanation of electron-deficient alkenes, Chem. Sci., 2013, 4, 2844.

(Continued)

*Primary Examiner* — Nizal S Chandrakumar

(74) *Attorney, Agent, or Firm* — Emory Patent Group

(57) ABSTRACT

This disclosure relates to chimeric compounds and methods for managing neurological conditions. In certain embodiments, the compound comprises a chemical structure of a monoamine reuptake inhibitor conjugated to a chemical structure of a histone deacetylase inhibitor. In certain embodiments, this disclosure relates to methods of treating or preventing a neurological disorder, mental disorder or depression comprising administering an effective amount of a compound disclosed herein to a subject in need thereof.

12 Claims, 7 Drawing Sheets

(56) References Cited

OTHER PUBLICATIONS

Zhu et al. Discovery of Novel Hydroxamates as Highly Potent Tumor Necrosis Factor-r Converting Enzyme Inhibitors: Part IsDiscovery of Two Binding Modes, J. Med. Chem. 2008, 51, 725-736.
Meanwell et al. Synopsis of Some Recent Tactical Application of Bioisosteres in Drug Design, | J. Med. Chem. 2011, 54, 2529-259.
Subbaiah et al. Bioisosteres of the Phenyl Ring: Recent Strategic Applications in Lead Optimization and Drug Design, J. Med. Chem. 2021, 64, 14046-14128.

* cited by examiner

HM2-R

HM2-S

HM3-R

HM3-S

HM3a-R

HM3a-S

Fluoxetine

Paroxetine

Sertraline

Escitalopram

Venlafaxine (SNRI)

Milnacipran (SNRI)

Duloxetine (SNRI)

Atomoxetine (NRI)

RB-513

CHIMERIC COMPOUNDS AND METHODS OF MANAGING NEUROLOGICAL DISORDERS OR CONDITIONS

CROSS-REFERENCE TO RELATED APPLICATIONS

This application is the National Stage of International Application No. PCT/US2020/019707, which claims the benefit of U.S. Provisional Application No. 62/810,009 filed Feb. 25, 2019. The entirety of each of these applications is hereby incorporated by reference for all purposes.

BACKGROUND

Depression is a mood disorder causing aversion to activity that can affect thoughts, behavior, feelings and sense of well-being. To treat depression effectively, antidepressants are commonly administered concurrently with psychotherapy. Commonly used antidepressants are selective serotonin reuptake inhibitors (SSRIs), as they have relatively benign side effects. SSRIs work by inhibiting reuptake of serotonin (5-HT) by presynaptic neurons (blocking the serotonin transporter, SERT) in the brain, thereby prolonging and increasing the effect of the serotonin that has been released. Current drugs are not universally effective with many patients eventually experiencing drug resistance. Moreover, the patient may experience a significant delay in the onset of therapeutic action or adverse side effects including GI distress and sexual dysfunction. Thus, there is a need identify improved therapies.

Covington et al. report hippocampal-dependent antidepressant-like activity of histone deacetylase inhibition. Neurosci Lett, 2011, 493(3): 122-126.

Jochems et al. report antidepressant-like properties of histone deacetylase 6 (HDAC6) selective inhibitors with improved brain bioavailability. J Neuropsychopharmacology, 2014, 39, 389-400.

Duan et al. report the synthesis of tranylcypromine derivatives as novel LSD1/HDACs dual inhibitors for cancer treatment. European Journal of Medicinal Chemistry, 2017, 140, 392-402.

Wang et al. report rhodium-catalyzed enantioselective cyclopropanation of electron deficient alkene. Chem Sci. 2013, 4(7): 2844-2850. See also WO 2012/145234 and U.S. Pat. No. 10,207,984.

References reported herein are not an admission of prior art.

SUMMARY

This disclosure relates to chimeric compounds and methods of managing neurological conditions. In certain embodiments, compounds comprise a chemical structure of a monoamine reuptake inhibitor conjugated to a chemical structure of a histone deacetylase inhibitor. In certain embodiments, this disclosure relates to methods of treating or preventing a neurological disorder, mental disorder, or depression comprising administering an effective amount of a compound disclosed herein to a subject in need thereof.

In certain embodiments, the chemical structure of the monoamine reuptake inhibitor is fluoxetine, atomoxetine, duloxetine, milnacipran, nomifensine, amitifadine, and the chemical structure of the histone deacetylase inhibitor comprises a N-hydroxybenzamide, a N-(2-aminophenyl)benzamide, or N-hydroxycinnamamide group. In certain embodiments, the chemical structure of a monoamine reuptake inhibitor conjugated to a chemical structure of a histone deacetylase inhibitor is through a linker.

In certain embodiments, the chemical structure of a monoamine reuptake inhibitor conjugated to a chemical structure of a histone deacetylase inhibitor are cyclopropyl amine derivatives comprising the following formula I:

Formula I

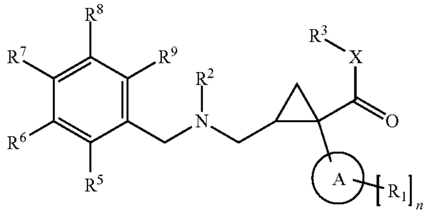

and salts, derivatives, prodrugs, or esters thereof wherein, the substituents are described herein.

In certain embodiments, the disclosure relates to compositions comprising a compound disclosed herein or one of the formula disclosed herein in greater than 60%, 70%, 80%, 90%, 95%, 98%, 99%, or 99.5% diastereomeric excess or enantiomeric excess. In certain embodiments, the disclosure relates to an isolated composition of a compound disclosed herein in substantially pure form.

In certain embodiments, the disclosure relates to a pharmaceutical composition comprising a compound disclosed herein or pharmaceutically acceptable salt or prodrug thereof and a pharmaceutically acceptable excipient. In certain embodiments, the disclosure relates to a pharmaceutical composition disclosed herein further comprising a second therapeutic agent.

In certain embodiments, the disclosure relates to methods of treating or preventing depression, a mental condition, or neurological disorder comprising administering an effective amount of a pharmaceutical composition disclosed herein to a subject diagnosed with, exhibiting symptoms of, or at risk for depression, a mental condition, or neurological disorder.

In certain embodiments, the disclosure relates to methods of preparing compounds disclosed herein comprising mixing the starting material and reagents under conditions such that the products are formed.

DETAILED DISCUSSION

Figure 1:
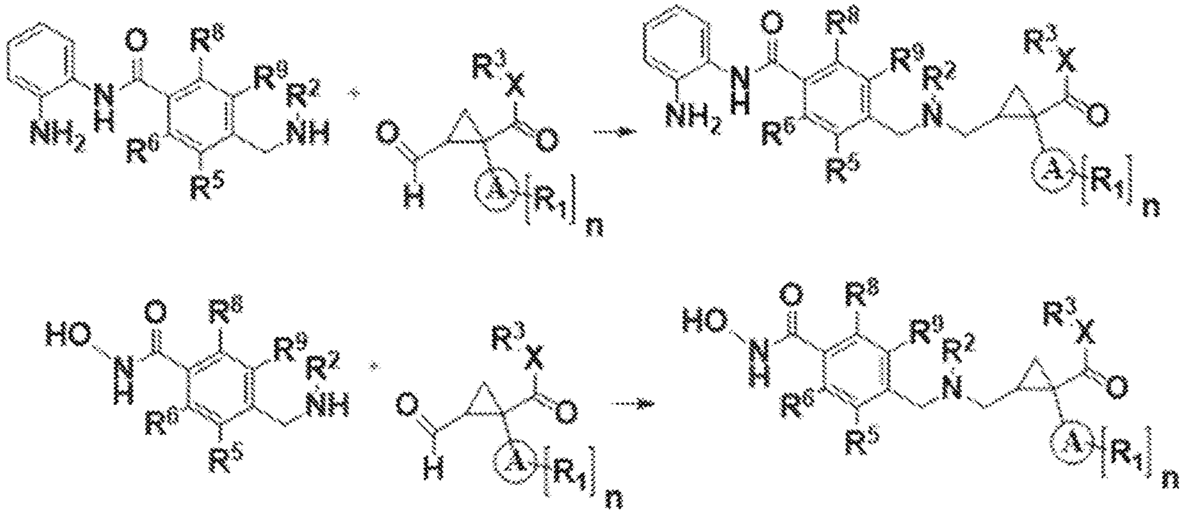
FIG. 1 shows a scheme illustrating the synthesis of cyclopropane amine derivatives.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

"Subject" refers any animal, preferably a human patient, livestock, or domestic pet.

A "chiral metal catalyst" refers to a catalytic metal complex where the ligands have one or more chiral centers. Examples include chiral 2-(2-aryl- or 2-alkyl-sufonylamino)phenyl-4-phenyl-1,3-oxazolines as ligands for copper-catalyzed enantioselective cyclopropanation reaction of olefins described in Ichiyanagi et al, Tetrahedron, 1997, 53(28), 9599-9610 and $Rh_2$(S-biTISP)$_2$, $Rh_2$(S-DOSP)$_4$, or $Rh_2$(S-PTAD)$_4$ catalysts as disclosed in Denton & Davies, Organic Letters, 2009, 11(4), 787-790, Davies et al., Tetrahedron Letters, 1996, 37(24) 4133-4136, and U.S. Pat. No. 7,385,064 hereby incorporated by reference. Chiral copper, rhodium, and ruthenium catalysts are representative of those contemplated by this disclosure. Typically, the metal-catalyzed cyclopropanation proceeds in a diastereoselective manner and is reported by the term "diastereomeric excess". When chiral ligands are incorporated into the catalysts, the cyclopropanation is also enantioselective, favoring one enantiomer of the product over the other, which is reported by the term "enantiomeric excess". Replacing the chiral ligands with their enantiomers will generate the enantiomer of the reaction product. The terms "enantiomeric excess" or "diastereomeric excess" refer to quantitative amounts of the respective isomers, i.e., the excess in terms of the diastereomers formed, or the excess in terms of the enantiomers formed. These amounts can be determined or approximated by methods well known in the art.

As used herein, "alkyl" means a noncyclic straight chain or branched, unsaturated or saturated hydrocarbon such as those containing from 1 to 10 carbon atoms, while the term "lower alkyl" or "$C_{1-4}$alkyl" has the same meaning as alkyl but contains from 1 to 4 carbon atoms. The term "higher alkyl" has the same meaning as alkyl but contains from 7 to 20 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Aryl" means an aromatic, carbocyclic, monocyclic or polycyclic ring such as phenyl or naphthyl. Polycyclic ring systems may, but are not required to, contain one or more non-aromatic rings, as long as one of the rings is aromatic.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Heterocarbocycles" or "heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, oxiranyl, oxetanyl, tetrahydrofuranyl, tetrahydropyranyl, tetrahydropyridinyl, tetrahydrothiophenyl, tetrahydrothiopyranyl, tetrahydropyrimidinyl, tetrahydrothiophenyl, tetrahydrothiopyranyl, and the like.

As used herein, "heteroaryl" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isoxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

"Alkylthio" refers to an alkyl group as defined above with the indicated number of carbon atoms attached through a sulfur bridge. An example of an alkylthio is methylthio, (i.e., $-S-CH_3$).

"Alkoxy" refers to an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylamino" refers an alkyl group as defined above with the indicated number of carbon atoms attached through an amino bridge. An example of an alkylamino is methylamino, (i.e., —NH—CH3).

"Alkanoyl" refers to an alkyl as defined above with the indicated number of carbon atoms attached through a carbonyl bride (i.e., —(C═O)alkyl).

"Alkylsulfonyl" refers to an alkyl as defined above with the indicated number of carbon atoms attached through a sulfonyl bridge (i.e., $-S(=O)_2$alkyl) such as mesyl and the like, and "Arylsulfonyl" refers to an aryl attached through a sulfonyl bridge (i.e., $-S(=O)_2$aryl).

"Alkylsulfamoyl" refers to an alkyl as defined above with the indicated number of carbon atoms attached through a sulfamoyl bridge (i.e., $-NHS(=O)_2$alkyl), and an "arylsulfamoyl" refers to an alkyl attached through a sulfamoyl bridge (i.e., (i.e., $-NHS(=O)_2$aryl).

"Alkylsulfinyl" refers to an alkyl as defined above with the indicated number of carbon atoms attached through a sulfinyl bridge (i.e. —S(═O)alkyl).

The term "substituted" refers to a molecule wherein at least one hydrogen atom is replaced with a substituent. When substituted, one or more of the groups are "substituents." The molecule may be multiply substituted. In the case of an oxo substituent ("═O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, $-NR_aR_b$, $-NR_aC(=O)R_b$, $-NR_aC(=O)NR_aNR_b$, $-NR_aC(=O)OR_b$, $-NR_aSO_2R_b$, $-C(=O)R_a$, $-C(=O)OR_a$, $-C(=O)NR_aR_b$, $-OC(=O)NR_aR_b$, —OR═, $-SR_a$, $-SOR_a$, $-S(=O)_2R_a$, $-OS(=O)_2R_a$ and $-S(=O)_2OR_a$. $R_a$ and $R_b$ in this context may be the same or different and independently hydrogen, halogen hydroxyl, alkyl, alkoxy, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In preferred embodiment the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

A "mental disorder" or "mental illness" or "mental disease" or "psychiatric or neuropsychiatric disease or illness or disorder" refers to mood disorders (e.g., depression, mania, and bipolar disorders), psychotic disorders (e.g., schizophrenia, schizoaffective disorder, schizophreniform disorder, delusional disorder, brief psychotic disorder, and shared psychotic disorder), personality disorders, anxiety disorders (e.g., obsessive-compulsive disorder) as well as other mental disorders such as substance-related disorders, childhood disorders, dementia, autistic disorder, adjustment disorder, delirium, multi-infarct dementia, and Tourette's disorder as described in Diagnostic and Statistical Manual of Mental Disorders, Fourth Edition, (DSM IV).

A "linking group" refers to any variety of molecular arrangements that can be used to bridge to molecular moieties together. An example formula may be $-R_n-$ wherein R is selected individually and independently at each occurrence as: $-CR_nR_n-$, $-CHR_n-$, $-CH-$, $-C-$, $-CH_2-$, $-C(OH)R_n$, $-C(OH)(OH)-$, $-C(OH)H$, $-C(Hal)R_n-$, $-C(Hal)(Hal)$-, $-C(Hal)H-$, $-C(N_3)R_n-$, $-C(CN)R_n-$, $-C(CN)(CN)-$, $-C(CN)H-$, $-C(N_3)(N_3)-$, $-C(N_3)H-$, $-O-$, $-S-$, $-N-$, $-NH-$, $-NR_n-$, $-(C{=}O)-$, $-(C{=}NH)-$, $-(C{=}S)-$, $-(C{=}CH_2)-$, which may contain single, double, or triple bonds individually and independently between the R groups. If an R is branched with an $R_n$ it may be terminated with a group such as $-CH_3$, $-H$, $-CH{=}CH_2$, $-CCH$, $-OH$, $-SH$, $-NH_2$, $-N_3$, $-CN$, or -Hal, or two branched Rs may form a cyclic structure. It is contemplated that in certain instances, the total Rs or "n" may be less than 100 or 50 or 25 or 10. Examples of linking groups include bridging alkyl and alkoxyalkyl groups.

Development of Anti-Depressant, a Chimera of Monoamine Reuptake Inhibitor and Hydroxamic Acid or Benzamide Depression is associated with greater disability than are most other chronic illnesses and is a risk factor for mortality. Between 10-15% of severely depressed people eventually commit suicide, and depression predicts the later development of a number of medical conditions, including cardiac and cerebrovascular disease, hypertension, diabetes, obesity, dementia, and cancer. Depression also markedly increases mortality in patients who are medically ill and has been associated with decreased responses to pharmacological treatments for cancer and infectious disease. A recently identified link between depression and medical illnesses including cancer is inflammation. Correlations between depressive symptom severity and increases in peripheral biomarkers of inflammation have been observed in multiple studies and in a number of clinical populations.

Depression, fatigue and loss of energy are also common behavioral changes associated with elevated cytokines in patients with cancer and cancer survivors. Of relevance to the development of depression, inflammatory cytokines have been shown to interact with virtually every pathophysiologic domain relevant to depression including neurotransmitter metabolism, neuroendocrine function and neural plasticity.

Protein acetylation has significant effects on important post-translational modifications that regulates multiple cellular functions, including chromatin remodeling and transcriptional regulation, metabolism, and aging. In cells, protein acetylation is regulated by two classes of functionally antagonistic enzymes: the protein acetylases and deacetylases. Much research has focused on enzymes that modulate the acetylation of histones because these are major components of chromatin and have the important roles in vital cellular functions and in disease. Levels of histone acetylation depend on the activities of histone acetyl transferases (HATs) and histone deacetylases (HDACs). Acetylation of lysine residues, catalyzed by HATs, neutralizes the positive charges of ε-amino groups on lysine residues, relaxes chromatin structure, and increases accessibility for the transcription machinery. Conversely, removal of acetyl groups from histones and other nuclear proteins by HDACs induces chromatin condensation and transcriptional repression. In other words, HDACs function to remove acetyl groups from histone tails that tighten the bonds between the histone lysines and the DNA phosphate backbone leaving no room for proteins necessary for transcription. In addition to histones, HDAC can modulate the function of many other proteins involved in the regulation of cell survival and proliferation, angiogenesis, inflammation, and immunity. Moreover, since HDACs play an important role in the regulation of gene expression, it is no surprise that deregulated HDAC activity is associated with many different diseases, especially, cancers, inflammation, and depression and is thus an attractive drug target.

Recently, the superfamily of HDACs has been recognized as an important therapeutic application for a broad range of human disorders, particularly for cancer treatment and as a potential treatment for neuropsychiatric disorders. Histone acetylation contributes to the transcriptional activation process by relaxing a repressive chromatin state, which facilitates the sequestration of the basal transcriptional machinery. Furthermore, expression levels of various HDACs are modulated by antidepressants and mood stabilizers in neuronal and nonneuronal tissue culture systems. Therefore, histone acetylation may represent a key target for antidepressant action. Aberrant activity of HDACs has been found in the nucleus accumbens of depressed humans leading to development of histone deacetylase inhibitors (HDACis). HDACis enhance histone acetylation, resulting in inducing chromatin relaxation, modulation of gene expression, and reversing the epigenetic changes.

A clinical trial was performed to evaluate vorinostat for the treatment of recurrent glioblastomas (GBM). Among the pleiotropic effects of HDAC inhibitors is the ability to attenuate inflammation, an action seen at concentrations lower than those required to slow cancer cell growth. GBM is frequently associated with neuroinflammation, which is thought to have pro-tumorigenic effects. Hypoxic and necrotic regions of GBMs are most highly associated with inflammatory cell infiltrates, and gene expression profiling reveals a signature associated with hypoxia-inducible genes involved in angiogenesis and inflammation. Such changes are associated with recruitment of macrophages along a hypoxia-mediated chemotactic gradient. Macrophages recruited to hypoxic sites exert tumor-promoting effects through the expression of genes with mitogenic, angiogenic, and migration/invasion stimulating properties. Abrogating inflammatory changes associated with GBM might reduce or eliminate access to these tumor-promoting effects. Another intriguing effect of HDACis as anticancer agents might be their mood-enhancing, potentially anti-depressant, properties. In mice, decreased histone acetylation in key mood-relevant genes was found following chronic social defeat stress, a mouse model of depression. Similar findings were observed in depressed humans on post-mortem exam. Moreover, infusion of HDACis into the brain of mice exposed to chronic social defeat exerted potent antidepressant effects. These findings are especially relevant, given the high frequency of depression (~40%) in brain tumor patients. In this patient population, depression is consistently associated with cognitive impairment, reduced physical function and poor quality-of-life. Anti-depressant effects of HDACis may be due to their anti-inflammatory properties, given recent data implicating inflammation in the development of depression including the identification of activated microglia in postmortem brain of depressed individuals.

During the clinical trial, levels of depression were assessed using the Inventory of Depressive Symptomatology-Self Report (IDS-SR) to determine whether vorinostat alters the severity of depressive symptoms among GBM patients. With only 7 days' of vorinostat treatment, IDS-SR scores were improved in 67% of the GBM patients. Although vorinostat showed promising effects as an anti-depressant, its side effect is fatigue that is shown in most patients who are on vorinostat treatment for more than 3 weeks. While the strong HDAC inhibitory effect of vorinostat is appreciated as a cancer therapeutic drug, it may be necessary to reduce the strong HDACi activity for antidepressant use to avoid the fatigue inducing effect.

Serotonin (SE) and Norepinephrine (NE) in the brain were recognized as the main neurotransmitters involved in the modulation of endogenous pain mechanism. Based on the clinical results, it is possible that increased concentration of both SE and NE would enhance the pain suppression via multiple postsynaptic receptor-mediated mechanisms. There are three different kinds of monoamine neurotransmitters (SE, NE and Dopamine (DA)) in the human brain that transmit nerve impulses from presynaptic neurons to postsynaptic neurons. When an impulse gets transmitted, neurotransmitters will be carried back into the presynaptic neuron via monoamine transporter proteins; Serotonin Transporter (SERT), Norepinephrine Transporter (NET) and Dopamine Transporter (DAT). These transporters have been shown to modulate sleep, mood, emotion and appetite. Many classes of clinical drugs target these three transporters and thereby have been classified into many groups based on their ability to selectively inhibit serotonin and/or noradrenaline and/or dopamine reuptake into the presynaptic neurons. Monoamine transporter inhibitors are an established drug class that have proven utility for the treatment of a number of the central nervous system (CNS) disorders, especially major depression disorder. Selective serotonin reuptake inhibitors (SSRIs), selective noradrenalin reuptake inhibitors (NARIs), dual SERT/NET reuptake inhibitors (SNRIs) such as duloxetine and milnacipran, dual NET/DAT reuptake inhibitors (NDRIs), and triple reuptake inhibitors (TRIs) were found to be effective in treating neuropathic pain but they also showed some adverse side effects such as nausea, vomiting, and dry mouth, but not fatigue.

Antidepressants as a Combination of Histone Deacetylase Inhibitors (HDACis) and Monoamine Reuptake Inhibitors Although HDACis have potential to be an effective antidepressant, their fatigue-inducing effect interferes with their clinical path as anti-depressants. On the other hand, monoamine reuptake inhibitors have shown limited efficacy in depression patients. In order to develop a class of antidepressants with improved efficacy, it was hypothesized that a class of molecules with $Zn^{2+}$ chelating motif of HDACis and the cyclopropyl ring of SNRIs could be effective antidepressants. Furthermore, an additional hypothesis was that the bioactivity for both enantiomers would be considerably different because of the difference in their 3-D formation in the receptor active site, which can be exploited to achieve the selectivity between two subtypes. Therefore, for development of multi-functional antidepressants, two materials, asymmetric cyclopropane aldehyde compounds and hydroxamic acid/2-aminobenzamide chelator, were combined to investigate antidepressants with better efficacy. Asymmetric cyclopropanes could relieve neuropathic pain while possibly avoiding adverse effects or minimizing side effects by controlling monoamine reuptake in nerve cell; hydroxamic acid and 2-aminobenzamide chelator would have a significant effect on antidepressant activity by inhibiting histone deacetylation as chelating $Zn^{2+}$ ions.

Figure 2A:
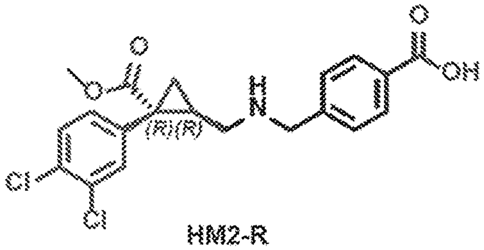
FIG. 2A illustrates certain embodiments of this disclosure.
Figure 2A:
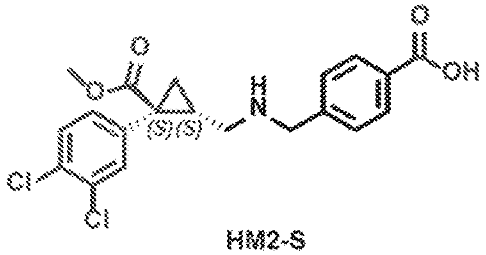
Figure 2A:
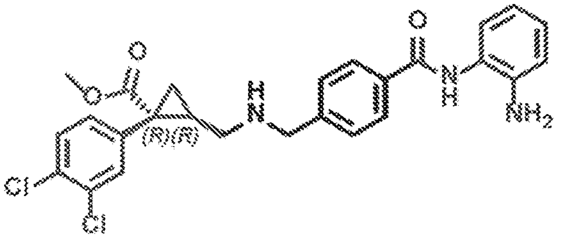
Figure 2A:
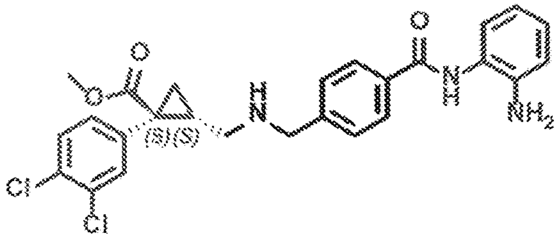
Figure 2A:
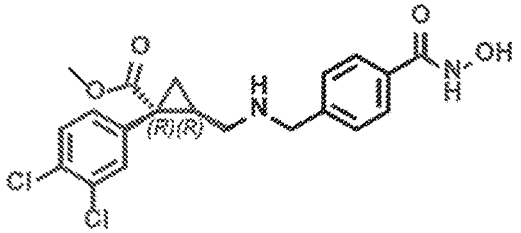
Figure 2A:
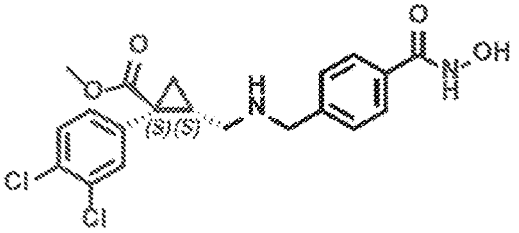
Figure 2B:
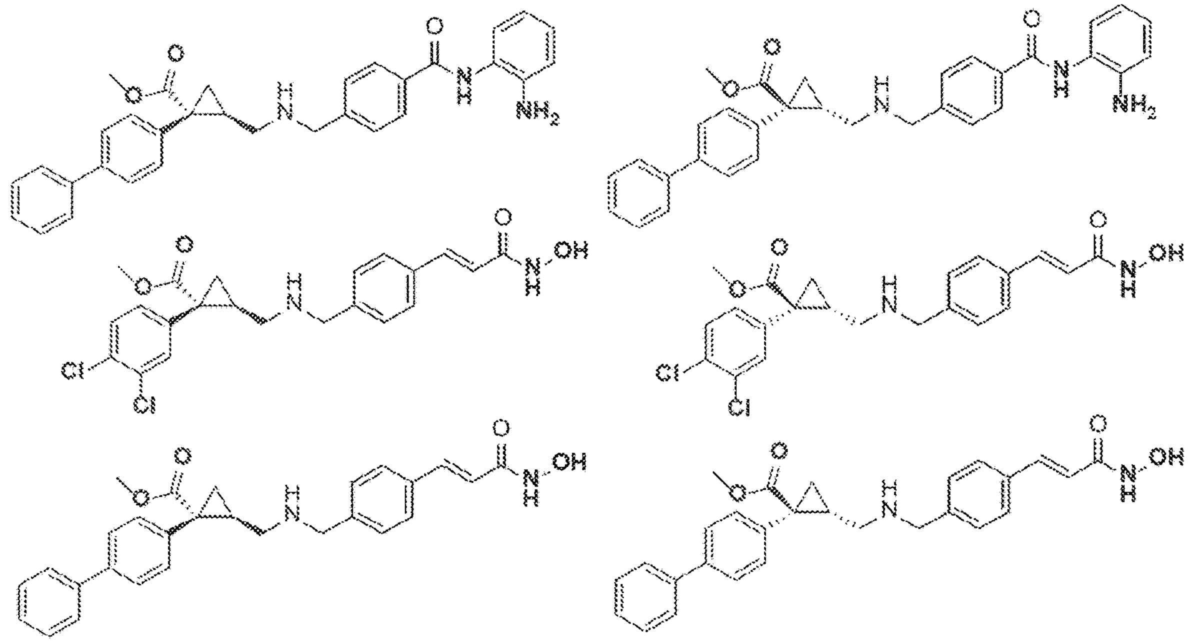
FIG. 2B illustrates certain embodiments of this disclosure.

Multifunctional antidepressants were designed with asymmetric cyclopropanes as monoamine reuptake inhibitors, as well as hydroxamic acid and 2-aminobenzamide as $Zn^{2+}$ chelator as HDACis. The structures of chiral cyclopropane scaffolds are shown in FIGS. 2A and 2B. The in vitro screenings of the compounds are performed to determine their HDAC inhibitory activity and monoamine reuptake inhibitory activity.

Chimeric Compounds

In certain embodiments, the chimeric compound comprises a chemical structure of a monoamine reuptake inhibitor conjugated to a chemical structure of a histone deacetylase inhibitor. In certain embodiments, the chimeric compound is any compound disclosed herein optionally substituted with one or more substituent, derivative, ester, or salt thereof.

In certain embodiments, the chemical structure of a monoamine reuptake inhibitor conjugated to a chemical structure of a histone deacetylase inhibitor is any of the compounds disclosed herein such a cyclopropyl amine derivative comprising the following formula I:

Formula I

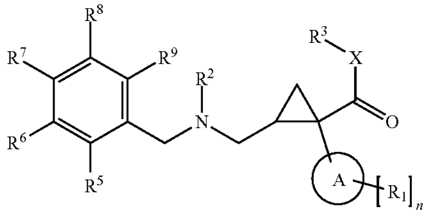

and salts, derivatives, prodrugs, or esters thereof wherein,

A ring is a carbocyclyl, aryl, or heterocyclyl;

n is 0, 1, 2, 3, 4, or 5;

X is C, O, S, $NR^4$;

$R^1$ is alkyl, halogen, nitro, cyano, hydroxy, amino, mercapto, formyl, alkanoyl, carboxy, carbamoyl, alkoxy, alkylthio, alkylamino, $(alkyl)_2$amino, alkylsulfinyl, alkylsulfonyl, arylsulfonyl, carbocyclyl, aryl, or heterocyclyl, wherein $R^1$ is optionally substituted with one or more, the same or different, $R^{10}$;

$R^2$ is hydrogen, alkyl, halogen, nitro, cyano, hydroxy, amino, mercapto, formyl, alkanoyl, carboxy, carbamoyl, alkoxy, alkylthio, alkylamino, $(alkyl)_2$amino, alkylsulfinyl, alkylsulfonyl, arylsulfonyl, carbocyclyl, aryl, or heterocyclyl, wherein $R^2$ is optionally substituted with one or more, the same or different, $R^{10}$;

$R^3$ is hydrogen, alkyl, halogen, nitro, cyano, hydroxy, amino, mercapto, formyl, alkanoyl, carboxy, carbamoyl, alkoxy, alkylthio, alkylamino, $(alkyl)_2$amino, alkylsulfinyl, alkylsulfonyl, arylsulfonyl, carbocyclyl, aryl, or heterocyclyl, wherein $R^3$ is optionally substituted with one or more, the same or different, $R^{10}$;

$R^4$ is hydrogen, alkyl, hydroxy, amino, formyl, carbocyclyl, aryl, or heterocyclyl, wherein $R^4$ is optionally substituted with one or more, the same or different, $R^{10}$;

$R^5$, $R^6$, $R^7$, $R^8$, and $R^9$ are, individually and independently, alkyl, halogen, nitro, cyano, hydroxy, amino, mercapto, formyl, alkanoyl, carboxy, carbamoyl, alkoxy, alkylthio, alkylamino, $(alkyl)_2$amino, alkylsulfinyl, alkylsulfonyl, arylsulfonyl, carbocyclyl, aryl, or heterocyclyl, wherein $R^5$, $R^6$, $R^7$, $R^8$, and $R^9$ are optionally substituted with one or more, the same or different, $R^{10}$;

$R^{10}$ is alkyl, halogen, nitro, cyano, hydroxy, amino, mercapto, formyl, alkanoyl, carboxy, carbamoyl, alkoxy, alkylthio, alkylamino, $(alkyl)_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$; and $R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^7$ is —(C═O)$YR^{12}$, wherein

Y is C, O, S, $NR^4$;

$R^4$ is hydrogen or alkyl;

$R^{12}$ is hydrogen, alkyl, halogen, nitro, cyano, hydroxy, amino, mercapto, formyl, alkanoyl, carboxy, carbamoyl, alkoxy, alkylthio, alkylamino, $(alkyl)_2$amino, alkylsulfinyl, alkylsulfonyl, arylsulfonyl, carbocyclyl, aryl, or heterocyclyl, wherein $R^{12}$ is optionally substituted with one or more, the same or different, $R^{20}$; and $R^{20}$ is alkyl, halogen, nitro, cyano, hydroxy, amino, mercapto, formyl, alkanoyl, carboxy, carbamoyl, alkoxy, alkylthio, alkylamino, $(alkyl)_2$amino, alkylsulfinyl, alkylsulfonyl, arylsulfonyl, carbocyclyl, aryl, or heterocyclyl, wherein $R^{20}$ is optionally substituted with one or more, the same or different, $R^{21}$; and $R^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, Y is NH, and $R^{12}$ is hydroxy or Y is NH and $R^{12}$ is 2-aminophen-1-yl.

In certain embodiments, $R^7$ is —CH═CH—(C═O)$YR^{12}$, wherein

Y is C, O, S, $NR^4$;

$R^4$ is hydrogen or alkyl;

$R^{12}$ is hydrogen, alkyl, halogen, nitro, cyano, hydroxy, amino, mercapto, formyl, alkanoyl, carboxy, carbamoyl, alkoxy, alkylthio, alkylamino, $(alkyl)_2$amino, alkylsulfinyl, alkylsulfonyl, arylsulfonyl, carbocyclyl, aryl, or heterocyclyl, wherein $R^{12}$ is optionally substituted with one or more, the same or different, $R^{20}$; and $R^{20}$ is alkyl, halogen, nitro, cyano, hydroxy, amino, mercapto, formyl, alkanoyl, carboxy, carbamoyl, alkoxy, alkylthio, alkylamino, $(alkyl)_2$amino, alkylsulfinyl, alkylsulfonyl, arylsulfonyl, carbocyclyl, aryl, or heterocyclyl, wherein $R^{20}$ is optionally substituted with one or more, the same or different, $R^{21}$; and $R^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, Y is NH, and $R^{12}$ is hydroxy or Y is NH and $R^{12}$ is 2-aminophen-1-yl.

In certain embodiments, the A ring is aryl or heteroaryl; n is 0, 1, 2, or 3; and X is oxygen.

In certain embodiments, the A ring is aryl or heteroaryl; n is 0, 1, 2, or 3; X is oxygen; $R^1$ is hydrogen, alkyl, halogen, nitro, cyano, hydroxy, amino, mercapto, formyl, alkanoyl, carboxy, carbamoyl, alkoxy, alkylthio, alkylamino, $(alkyl)_2$amino, alkylsulfinyl, alkylsulfonyl, arylsulfonyl, carbocyclyl, aryl, or heterocyclyl, wherein $R^1$ is optionally substituted with one or more, the same or different, $R^{10}$; $R^2$ is hydrogen or alkyl; and $R^3$ is hydrogen or alkyl.

In certain embodiments, the A ring is aryl or heteroaryl.

In certain embodiments, the A ring is aryl or heteroaryl and X is oxygen or $NR^4$.

In certain embodiments, the A ring is aryl or heteroaryl, $R^3$ is hydrogen or $C_{1-4}$alkyl and X is oxygen or $NR^4$.

In certain embodiments, the A ring is aryl or heteroaryl, $R^2$ is hydrogen or $C_{1-4}$alkyl, and X is oxygen or $NR^4$.

In certain embodiments, the A ring is aryl or heteroaryl, $R^1$ is a hydrogen, halogen, or alkoxy, X is oxygen, and $R^2$ is hydrogen or $C_{1-4}$alkyl.

In certain embodiments, the A ring is aryl or heteroaryl, and X is oxygen or $NR^4$.

In certain embodiments, the A ring is phenyl, naphthyl or biphenyl.

In certain embodiments, the A ring is phenyl, naphthyl or biphenyl and X is oxygen or $NR^4$.

In certain embodiments, the A ring is phenyl, naphthyl or biphenyl, $R^3$ is hydrogen or $C_{1-4}$alkyl and X is oxygen or $NR^4$.

In certain embodiments, the A ring is phenyl, naphthyl or biphenyl, Y is $NR^4$ or oxygen and X is oxygen or $NR^4$.

In certain embodiments, the A ring is phenyl, naphthyl or biphenyl, $R^2$ is hydrogen or $C_{1-4}$alkyl, Y is $NR^4$, and X is oxygen.

In certain embodiments, the A ring is phenyl, naphthyl or biphenyl, $R^1$ is a hydrogen, halogen, or alkoxy, X is oxygen, and $R^2$ is hydrogen or $C_{1-4}$alkyl.

In certain embodiments, X is oxygen.

In certain embodiments, X is $NR^4$, wherein $R^4$ is hydrogen or $C_{1-4}$alkyl.

In certain embodiments, $R^3$ is hydrogen or $C_{1-4}$alkyl.

In certain embodiments, $R^3$ is methyl or ethyl.

In certain embodiments, $R^2$ is hydrogen or $C_{1-4}$alkyl.

In certain embodiments, $R^2$ is methyl or ethyl.

In certain embodiments, the disclosure relates to compounds comprising the following formula IA:

Formula IA

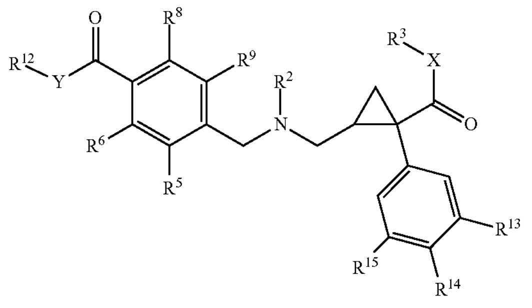

and salts, derivatives, prodrugs, or esters thereof wherein,

X is C, O, S, $NR^4$;

Y is C, O, S, $NR^4$;

$R^2$ is hydrogen, alkyl, halogen, nitro, cyano, hydroxy, amino, mercapto, formyl, alkanoyl, carboxy, carbamoyl, alkoxy, alkylthio, alkylamino, $(alkyl)_2$amino, alkylsulfinyl, alkylsulfonyl, arylsulfonyl, carbocyclyl, aryl, or heterocyclyl, wherein $R^2$ is optionally substituted with one or more, the same or different, $R^{10}$;

$R^3$ is hydrogen, alkyl, halogen, nitro, cyano, hydroxy, amino, mercapto, formyl, alkanoyl, carboxy, carbamoyl, alkoxy, alkylthio, alkylamino, $(alkyl)_2$amino, alkylsulfinyl, alkylsulfonyl, arylsulfonyl, carbocyclyl, aryl, or heterocyclyl, wherein $R^3$ is optionally substituted with one or more, the same or different, $R^{10}$;

$R^4$ is hydrogen, alkyl, hydroxy, amino, formyl, carbocyclyl, aryl, or heterocyclyl, wherein $R^4$ is optionally substituted with one or more, the same or different, $R^{10}$;

$R^5$, $R^6$, $R^8$, and $R^9$ are, individually and independently, alkyl, halogen, nitro, cyano, hydroxy, amino, mercapto, formyl, alkanoyl, carboxy, carbamoyl, alkoxy, alkylthio, alkylamino, $(alkyl)_2$amino, alkylsulfinyl, alkylsulfonyl, arylsulfonyl, carbocyclyl, aryl, or heterocyclyl, wherein $R^5$, $R^6$, $R^8$, and $R^9$ are optionally substituted with one or more, the same or different, $R^{10}$;

$R^{10}$ is alkyl, halogen, nitro, cyano, hydroxy, amino, mercapto, formyl, alkanoyl, carboxy, carbamoyl, alkoxy, alkylthio, alkylamino, $(alkyl)_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$; and $R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{12}$ is hydrogen, alkyl, halogen, nitro, cyano, hydroxy, amino, mercapto, formyl, alkanoyl, carboxy, carbamoyl, alkoxy, alkylthio, alkylamino, $(alkyl)_2$amino, alkylsulfinyl, alkylsulfonyl, arylsulfonyl, carbocyclyl, aryl, or heterocyclyl, wherein $R^{12}$ is optionally substituted with one or more, the same or different, $R^{20}$; and $R^{13}$, $R^{14}$, and $R^{15}$ are, individually and independently, alkyl, halogen, nitro, cyano, hydroxy, amino, mercapto, formyl, alkanoyl, carboxy, carbamoyl, alkoxy, alkylthio, alkylamino, $(alkyl)_2$amino, alkylsulfinyl, alkylsulfonyl, arylsulfonyl, carbocyclyl, aryl, or heterocyclyl, wherein $R^{13}$, $R^{14}$, and $R^{15}$ are optionally substituted with one or more, the same or different, $R^{20}$; and $R^{20}$ is alkyl, halogen, nitro, cyano, hydroxy, amino, mercapto, formyl, alkanoyl, carboxy, carbamoyl, alkoxy, alkylthio, alkylamino, $(alkyl)_2$amino, alkylsulfinyl, alkylsulfonyl, arylsulfonyl, carbocyclyl, aryl, or heterocyclyl, wherein $R^{20}$ is optionally substituted with one or more, the same or different, $R^{21}$; and $R^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, Y is oxygen.

In certain embodiments, X is oxygen and Y is $NR^4$, wherein $R^4$ is hydrogen or $C_{1-4}$alkyl.

In certain embodiments, $R^3$ is hydrogen or $C_{1-4}$alkyl.

In certain embodiments, $R^3$ is methyl or ethyl.

In certain embodiments, $R^2$ is hydrogen or $C_{1-4}$alkyl.

In certain embodiments, $R^2$ is methyl or ethyl.

In certain embodiments, the disclosure relates to compounds comprising the following formula IB:

Formula IB

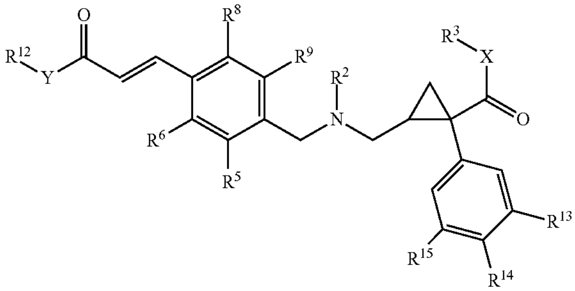

and salts, derivatives, prodrugs, or esters thereof wherein,

X is C, O, S, $NR^4$;

Y is C, O, S, $NR^4$;

$R^2$ is hydrogen, alkyl, halogen, nitro, cyano, hydroxy, amino, mercapto, formyl, alkanoyl, carboxy, carbamoyl, alkoxy, alkylthio, alkylamino, $(alkyl)_2$amino, alkylsulfinyl, alkylsulfonyl, arylsulfonyl, carbocyclyl, aryl, or heterocyclyl, wherein $R^2$ is optionally substituted with one or more, the same or different, $R^{10}$;

$R^3$ is hydrogen, alkyl, halogen, nitro, cyano, hydroxy, amino, mercapto, formyl, alkanoyl, carboxy, carbamoyl, alkoxy, alkylthio, alkylamino, $(alkyl)_2$amino, alkylsulfinyl, alkylsulfonyl, arylsulfonyl, carbocyclyl, aryl, or heterocyclyl, wherein $R^3$ is optionally substituted with one or more, the same or different, $R^{10}$;

$R^4$ is hydrogen, alkyl, hydroxy, amino, formyl, carbocyclyl, aryl, or heterocyclyl, wherein $R^4$ is optionally substituted with one or more, the same or different, $R^{10}$;

$R^5$, $R^6$, $R^8$, and $R^9$ are, individually and independently, alkyl, halogen, nitro, cyano, hydroxy, amino, mercapto, formyl, alkanoyl, carboxy, carbamoyl, alkoxy, alkylthio, alkylamino, $(alkyl)_2$amino, alkylsulfinyl, alkylsulfonyl, arylsulfonyl, carbocyclyl, aryl, or heterocyclyl, wherein $R^5$, $R^6$, $R^8$, and $R^9$ are optionally substituted with one or more, the same or different, $R^{10}$;

$R^{10}$ is alkyl, halogen, nitro, cyano, hydroxy, amino, mercapto, formyl, alkanoyl, carboxy, carbamoyl, alkoxy, alkylthio, alkylamino, $(alkyl)_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$; and $R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{12}$ is hydrogen, alkyl, halogen, nitro, cyano, hydroxy, amino, mercapto, formyl, alkanoyl, carboxy, carbamoyl, alkoxy, alkylthio, alkylamino, $(alkyl)_2$amino, alkylsulfinyl, alkylsulfonyl, arylsulfonyl, carbocyclyl, aryl, or heterocyclyl, wherein $R^{12}$ is optionally substituted with one or more, the same or different, $R^{20}$; and $R^{13}$, $R^{14}$, and $R^{15}$ are, individually and independently, alkyl, halogen, nitro, cyano, hydroxy, amino, mercapto, formyl, alkanoyl, carboxy, carbamoyl, alkoxy, alkylthio, alkylamino, $(alkyl)_2$amino, alkylsulfinyl, alkylsulfonyl, arylsulfonyl, carbocyclyl, aryl, or heterocyclyl, wherein $R^{13}$, $R^{14}$, and $R^{15}$ are optionally substituted with one or more, the same or different, $R^{20}$; and $R^{20}$ is alkyl, halogen, nitro, cyano, hydroxy, amino, mercapto, formyl, alkanoyl, carboxy, carbamoyl, alkoxy, alkylthio, alkylamino, $(alkyl)_2$amino, alkylsulfinyl, alkylsulfonyl, arylsulfonyl, carbocyclyl, aryl, or heterocyclyl, wherein $R^{20}$ is optionally substituted with one or more, the same or different, $R^{21}$; and $R^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, Y is NH, and $R^{12}$ is hydroxy or Y is NH and $R^{12}$ is 2-aminophen-1-yl.

In certain embodiments, Y is oxygen.

In certain embodiments, X is oxygen and Y is $NR^4$, wherein $R^4$ is hydrogen or $C_{1-4}$alkyl.

In certain embodiments, $R^3$ is hydrogen or $C_{1-4}$alkyl.

In certain embodiments, $R^3$ is methyl or ethyl.

In certain embodiments, $R^2$ is hydrogen or $C_{1-4}$alkyl.

In certain embodiments, $R^2$ is methyl or ethyl.

In certain embodiments, the disclosure relates to compounds comprising the following formula IC:

Formula IC

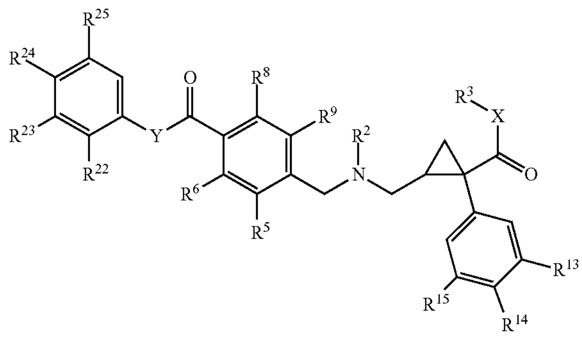

and salts, derivatives, prodrugs, or esters thereof wherein,

X is C, O, S, $NR^4$;

Y is C, O, S, $NR^4$;

$R^2$ is hydrogen, alkyl, halogen, nitro, cyano, hydroxy, amino, mercapto, formyl, alkanoyl, carboxy, carbamoyl, alkoxy, alkylthio, alkylamino, $(alkyl)_2$amino, alkylsulfinyl, alkylsulfonyl, arylsulfonyl, carbocyclyl, aryl, or heterocyclyl, wherein $R^2$ is optionally substituted with one or more, the same or different, $R^{10}$;

$R^3$ is hydrogen, alkyl, halogen, nitro, cyano, hydroxy, amino, mercapto, formyl, alkanoyl, carboxy, carbamoyl, alkoxy, alkylthio, alkylamino, $(alkyl)_2$amino, alkylsulfinyl, alkylsulfonyl, arylsulfonyl, carbocyclyl, aryl, or heterocyclyl, wherein $R^3$ is optionally substituted with one or more, the same or different, $R^{10}$;

$R^4$ is hydrogen, alkyl, hydroxy, amino, formyl, carbocyclyl, aryl, or heterocyclyl, wherein $R^4$ is optionally substituted with one or more, the same or different, $R^{10}$;

$R^5$, $R^6$, $R^8$, and $R^9$ are, individually and independently, alkyl, halogen, nitro, cyano, hydroxy, amino, mercapto, formyl, alkanoyl, carboxy, carbamoyl, alkoxy, alkylthio, alkylamino, $(alkyl)_2$amino, alkylsulfinyl, alkylsulfonyl, arylsulfonyl, carbocyclyl, aryl, or heterocyclyl, wherein $R^5$, $R^6$, $R^8$, and $R^9$ are optionally substituted with one or more, the same or different, $R^{10}$;

$R^{10}$ is alkyl, halogen, nitro, cyano, hydroxy, amino, mercapto, formyl, alkanoyl, carboxy, carbamoyl, alkoxy, alkylthio, alkylamino, $(alkyl)_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$; and $R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{13}$, $R^{14}$, and $R^{15}$ are, individually and independently, alkyl, halogen, nitro, cyano, hydroxy, amino, mercapto, formyl, alkanoyl, carboxy, carbamoyl, alkoxy, alkylthio, alkylamino, $(alkyl)_2$amino, alkylsulfinyl, alkylsulfonyl, arylsulfonyl, carbocyclyl, aryl, or heterocyclyl, wherein $R^{13}$, $R^{14}$, and $R^{15}$ are optionally substituted with one or more, the same or different, $R^{20}$; and $R^{20}$ is alkyl, halogen, nitro, cyano, hydroxy, amino, mercapto, formyl, alkanoyl, carboxy, carbamoyl, alkoxy, alkylthio, alkylamino, $(alkyl)_2$amino, alkylsulfinyl, alkylsulfonyl, arylsulfonyl, carbocyclyl, aryl, or heterocyclyl, wherein $R^{20}$ is optionally substituted with one or more, the same or different, $R^{21}$; and $R^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

$R^{22}$, $R^{23}$, $R^{24}$, and $R^{25}$ are, individually and independently, alkyl, halogen, nitro, cyano, hydroxy, amino, mercapto, formyl, alkanoyl, carboxy, carbamoyl, alkoxy, alkylthio, alkylamino, $(alkyl)_2$amino, alkylsulfinyl, alkylsulfonyl, arylsulfonyl, carbocyclyl, aryl, or heterocyclyl, wherein $R^{22}$, $R^{23}$, $R^{24}$, and $R^{25}$ are optionally substituted with one or more, the same or different, $R^{30}$; and $R^{30}$ is alkyl, halogen, nitro, cyano, hydroxy, amino, mercapto, formyl, alkanoyl, carboxy, carbamoyl, alkoxy, alkylthio, alkylamino, $(alkyl)_2$amino, alkylsulfinyl, alkylsulfonyl, arylsulfonyl, carbocyclyl, aryl, or heterocyclyl, wherein $R^{30}$ is optionally substituted with one or more, the same or different, $R^{31}$; and $R^{31}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, Y is NH, and $R^{12}$ is hydroxy or Y is NH and $R^{12}$ is 2-aminophen-1-yl. In certain embodiments, $R^{22}$ is an amino or a primary amine.

In certain embodiments, the disclosure relates to a compound of formula I, wherein formula IA is formula IIA, IIB, IIC or IID wherein:

formula IIA is,

Formula IIA

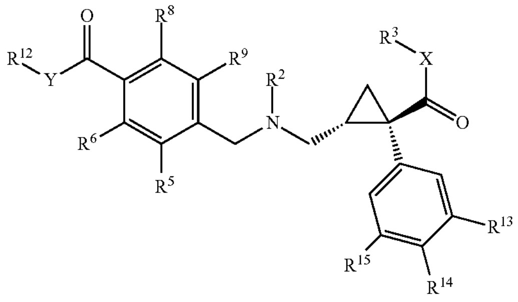

formula IIB is,

Formula IIB

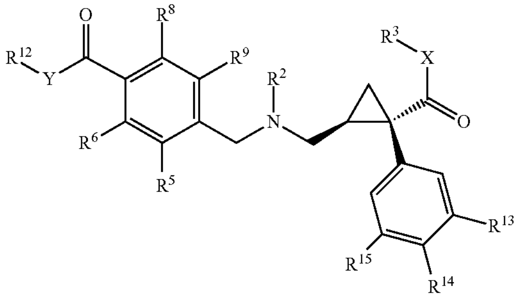

formula IIC is,

Formula IIC

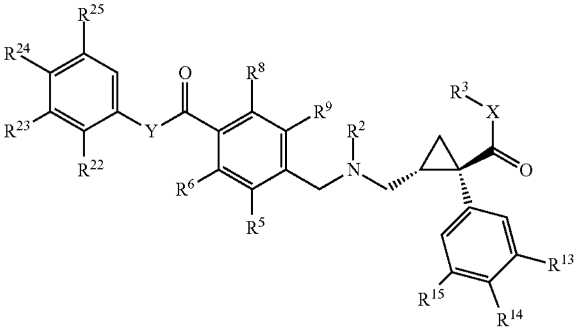

formula IID is,

Formula IID

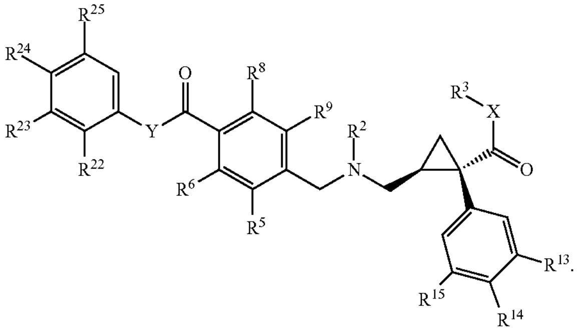

In certain embodiments, the disclosure relates to a compound of formula I, wherein formula IB is formula IIE or IIF wherein:

Formula IIE is,

Formula IIE

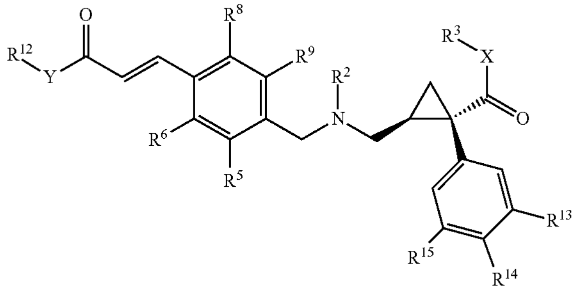

Formula IIF is,

Formula IIF

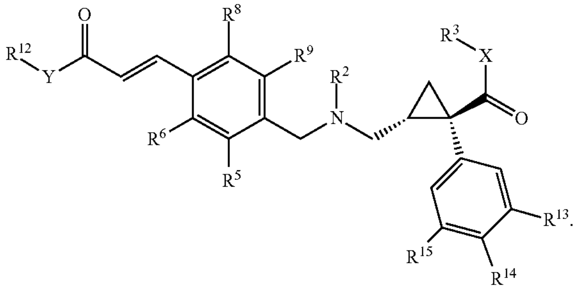

In certain embodiments, the disclosure relates to a compound of formula I, wherein formula IC is formula IIG or IIH wherein:

Formula IIG is,

Formula IIG

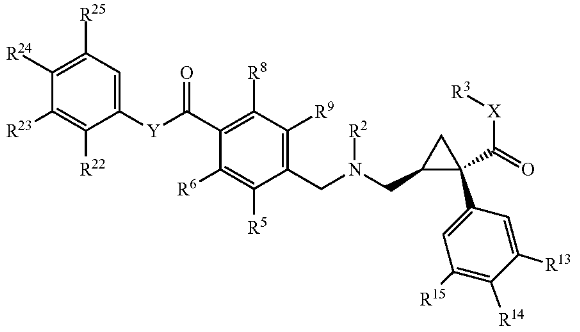

Formula IIH is,

Formula IIH

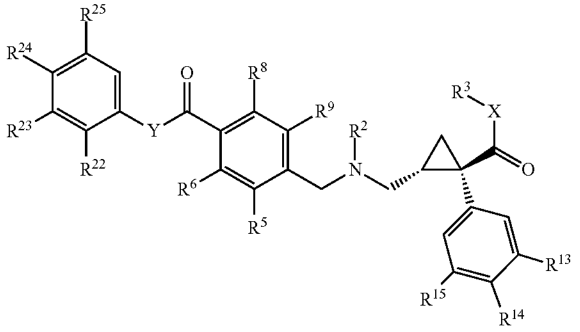

In certain embodiments, Y is NH, and $R^{12}$ is hydroxy or Y is NH and $R^{12}$ is 2-aminophen-1-yl. In certain embodiments, $R^{22}$ is primary amine.

In certain embodiments, the disclosure relates to compositions comprising a compound of formula IIA, IIB, IIC, IID, IIE, IIF, IIG, or IIH in greater than 60%, 70%, 80%, 90%, 95%, or 98% diastereomeric excess.

In some embodiments, the disclosure relates to a compound selected from:

(1R,2R)-methyl-2-(((4-((2-aminophenyl)carbamoyl)benzyl) amino)methyl)-1-(3,4 dichlorophenyl)cyclopropane-1-carboxylate, (1R,2R)-methyl-1-([1,1'-biphenyl]-4-yl)-2-(((4-((2-aminophenyl)carbamoyl)benzyl) amino)methyl)cyclopropane-1-carboxylate, (1R,2R)-methyl-1-(3,4-dichlorophenyl)-2-(((4-((E)-3-(hydroxyamino)-3-oxoprop-1-en-1-yl)benzyl)amino)methyl) cyclopropane-1-carboxylate, (1R,2R)-methyl-1-([1,1'-biphenyl]-4-yl)-2-(((4-((E)-3-(hydroxyamino)-3-oxoprop-1-en-1-yl)benzyl)amino)methyl) cyclopropane-1-carboxylate, (1S,2S)-methyl-2-(((4-((2-aminophenyl)carbamoyl)benzyl) amino)methyl)-1-(3,4-dichlorophenyl)cyclopropane-1-carboxylate, (1S,2S)-methyl-1-([1,1'-biphenyl]-4-yl)-2-(((4-((2-aminophenyl)carbamoyl)benzyl) amino)methyl)cyclopropane-1-carboxylate, (1S,2S)-methyl-1-(3,4-dichlorophenyl)-2-(((4-((E)-3-(hydroxyamino)-3-oxoprop-1-en-1-yl)benzyl)amino)methyl) cyclopropane-1-carboxylate, (1S,2S)-methyl-1-([1,1'-biphenyl]-4-yl)-2-(((4-((E)-3-(hydroxyamino)-3-oxoprop-1-en-1-yl)benzyl)amino)methyl) cyclopropane-1-carboxylate, 4-(((((1R,2R)-2-(3,4-dichlorophenyl)-2-(methoxycarbonyl) cyclopropyl)methyl) amino) methyl)benzoic acid, 4-(((((1S,2S)-2-(3,4-dichlorophenyl)-2-(methoxycarbonyl) cyclopropyl)methyl)amino) methyl)benzoic, (1S,2S)-methyl-1-(3,4-dichlorophenyl)-2-(((4-(hydroxycarbamoyl)benzyl)amino) methyl) cyclopropane-1-carboxylate, (1R,2R)-methyl-1-(3,4-dichlorophenyl)-2-(((4-(hydroxycarbamoyl)benzyl) amino)methyl) cyclopropane-1-carboxylate, or salts thereof.

Therapeutic Applications

In some embodiments, the disclosure relates to methods of treating or preventing neuropsychiatric disorders with pharmaceutical compositions disclosed herein administered to subject in need thereof. Examples of neuropsychiatric disorders include, but are not limited to, depression, major depression disorder, atypical depression, melancholic depression, postpartum depression, seasonal affective disorder.

Depression is a state of low mood and aversion to activity that can affect a person's thoughts, behavior, feelings and sense of well-being. While many people deal with periods of depression at points within their lives, for some it becomes an ongoing consistent problem in which they are clinically diagnosed with a depressive mood disorder.

In all these cases anti-depressants are used as part of the treatment strategy. The most commonly used anti-depressants are the SSRI, selective serotonin reuptake inhibitors, as they have relatively mild side effects, less toxic, and less prone to overdose than other types of anti-depressants. SSRIs work by inhibiting reuptake of serotonin (5-HT) by presynaptic neurons (blocking the serotonin transporter, SERT) in the brain, therefore prolonging and increasing the effect of the serotonin that has been released into the synaptic cleft and therefore on the postsynaptic neuron. Treatment strategies have focused on inhibiting 5-HT in combination with inhibition of other monoamine neurotransmitters as well, for example norepinephrine (by inhibiting NET) and dopamine (by inhibiting DAT). These drugs are known as SNRIs (5-HT and NE reuptake inhibitors) and SNDRIs (5-HT, NE, & DA reuptake inhibitors) in which the molecules inhibit the reuptake of multiple monoamine neurotransmitters, prolonging their effect. Multi-monoamine reuptake inhibitors do not work consistently for all patients, and like traditional SSRIs they suffer from a delayed onset in effectiveness, meaning the drug must be taken for multiple weeks before a clinical effect is seen.

Pharmaceutical Formulations

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When the compounds contain a hydrogen-donating heteroatom (e.g. NH), this disclosure contemplates salts and/or isomers formed by transfer of said hydrogen atom to a basic group or atom within the molecule, such as in the case of an amino acid.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as prodrugs can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids.

Pharmaceutical compositions for use in the present disclosure typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is again made to U.S. Pat. Nos. 6,372,778, 6,369,086, 6,369,087, and 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient and/or adjuvant, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g. about 10, 25, 50, 100, 200, 300 or 400 mg per unit dosage.

The compounds can be administered by a variety of routes including the oral, ocular, rectal, transdermal, subcutaneous, intravenous, intramuscular, spinal, epidural, or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. Nos. 6,372,778, 6,369,086, 6,369,087, and 6,372,733 and the further references mentioned above, as well as to the standard handbooks, such as the latest edition of Remington's Pharmaceutical Sciences.

For an oral administration form, the compound can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, the compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the disclosure or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

For subcutaneous, spinal, epidural, or intravenous administration, the compounds, if desired with the substances customary therefore such as solubilizers, emulsifiers or further auxiliaries are brought into solution, suspension, or emulsion. The compounds of formula I can also be lyophilized and the lyophilizates obtained used, for example, for the production of injection or infusion preparations. Suitable solvents are, for example, water, physiological saline solution or alcohols, e.g. ethanol, propanol, glycerol, sugar solutions such as glucose or mannitol solutions, or mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, the formulations may be prepared by mixing the compounds of formula I with a suitable non-irritating excipient, such as cocoa butter, synthetic glyceride esters or polyethylene glycols, which are solid at ordinary temperatures, but liquefy and/or dissolve in the rectal cavity to release the drug.

In certain embodiments, it is contemplated that these compositions can be extended release formulations. Typical extended release formations utilize an enteric coating. A barrier is applied to oral medication that controls the location in the digestive system where it is absorbed. Enteric coatings prevent release of medication before it reaches the small intestine. Enteric coatings may contain polymers of polysaccharides, such as maltodextrin, xanthan, scleroglucan dextran, starch, alginates, pullulan, hyaluronic acid, chitin, chitosan and the like; other natural polymers, such as proteins (albumin, gelatin etc.), poly-L-lysine; sodium poly (acrylic acid); poly(hydroxyalkylmethacrylates) (for example poly(hydroxyethylmethacrylate)); carboxypolymethylene (for example Carbopol™); carbomer; polyvinylpyrrolidone; gums, such as guar gum, gum arabic, gum karaya, gum ghatti, locust bean gum, tamarind gum, gellan gum, gum tragacanth, agar, pectin, gluten and the like; poly(vinyl alcohol); ethylene vinyl alcohol; polyethylene glycol (PEG); and cellulose ethers, such as hydroxymethylcellulose (HMC), hydroxyethylcellulose (HEC), hydroxypropylcellulose (HPC), methylcellulose (MC), ethylcellulose (EC), carboxyethylcellulose (CEC), ethylhydroxyethylcellulose (EHEC), carboxymethylhydroxyethylcellulose (CMHEC), hydroxypropylmethyl-cellulose (HPMC), hydroxypropylethylcellulose (HPEC) and sodium carboxymethylcellulose (Na CMC); as well as copolymers and/or (simple) mixtures of any of the above polymers. Certain of the above-mentioned polymers may further be crosslinked by way of standard techniques.

The choice of polymer will be determined by the nature of the active ingredient/drug that is employed in the composition of the disclosure as well as the desired rate of release. In particular, it will be appreciated by the skilled person, for example in the case of HPMC, that a higher molecular weight will, in general, provide a slower rate of release of drug from the composition. Furthermore, in the case of HPMC, different degrees of substitution of methoxy groups and hydroxypropoxy groups will give rise to changes in the rate of release of drug from the composition. In this respect, and as stated above, it may be desirable to provide compositions of the disclosure in the form of coatings in which the polymer carrier is provided by way of a blend of two or more polymers of, for example, different molecular weights in order to produce a particular required or desired release profile.

Combination Therapies

With regard to neuropsychiatric disorders, compounds disclosed herein may be administer in combinations with other psychiatric medications, such as antidepressants, anxiolytics, anticonvulsants, antipsychotics and stimulants such as anti-inflammatory agents.

Representative antidepressants include monoamine oxidase inhibitors (MAOIs), tricyclic antidepressants (TCAs), tetracyclic antidepressants (TeCAs), selective serotonin reuptake inhibitors (SSRIs), serotonin-norepinephrine reuptake inhibitors (SNRIs) and others.

Representative selective and non-selective MAOIs include benmoxin, hydralazine, iproclozide, iproniazid, isocarboxazid, isoniazid, mebanazine, nialamide, octamoxin, phenelzine, pheniprazine, phenoxypropazine, pivalylbenzhydrazine, procarbazine, safrazine, caroxazone, echinopsidine, furazolidone, linezolid, tranylcypromine, brofaromine, metralindole, minaprine, moclobemide, pirlindole, toloxatone, lazabemide, pargyline, rasagiline, selegiline, resveratrol, curcumin, catechin, desmethoxyyangonin, epicatechin, hydroxytyrosol, and piperine.

Representative TCAs include amitriptyline, amitriptylinoxide, butriptyline, clomipramine, demexiptiline, desipramine, dibenzepin, dimetacrine, dosulepin/dothiepin, doxepin, imipramine, imipramine oxide, lofepramine, melitracen, metapramine, nitroxazepine, nortriptyline, noxiptiline, pipofezine, propizepine, protriptyline, quinupramine, amineptine, iprindole, opipramol, tianeptine, trimipramine.

Representative TeCAs include, amoxapine, maprotiline, mazindol, mianserin, mirtazapine, setiptiline, and oxaprotiline.

Representative SSRIs include citalopram, dapoxetine, escitalopram, fluoxetine, fluvoxamine, indalpine, paroxetine, sertraline, and zimelidine.

Representative SNRIs include venlafaxine, desvenlafaxine, duloxetine, milnacipran, levomilnacipran, sibutramine, and bicifadine.

Other representative anti-depressants include mianserin, mirtazapine, atomoxetine, mazindol, reboxetine, viloxazine, bupropion, tianeptine, and agomelatine.

Representative anxiolytics include alprazolam, chlordiazepoxide, clonazepam, diazepam, lorazepam, buspirone, tandospirone, gepirone, hydroxyzine, and pregabalin.

Representative anticonvulsants include lithium, valproic acid, lamotrigine, carbamazepine, oxcarbazepine, and gabapentin.

Representative antipsychotics include haloperidol, droperidol, chlorpromazine, fluphenazine, perphenazine, prochlorperazine, thioridazine, trifluoperazine, mesoridazine, periciazine, promazine, triflupromazine, levomepromazine, promethazine, pimozide, chlorprothixene, clopenthixol, flupenthixol, thiothixene, zuclopenthixol, clozapine, olanzapine, risperidone, quetiapine, ziprasidone, amisulpride, asenapine, paliperidone, iloperidone, zotepine, sertindole, aripiprazole, bifeprunox, and cannabidiol.

Representative stimulants include caffeine nicotine, amphetamine, methamphetamine, methylenedioxymethamphetamine, troparil, methylphenidate, bupropion atomoxetine, reboxetine, modafinil, carphedon, and yohimbine.

Suitable anti-inflammatory compounds include both steroidal and non-steroidal structures. Suitable non-limiting examples of steroidal anti-inflammatory compounds are corticosteroids such as hydrocortisone, cortisol, hydroxyl triamcinolone, alpha-methyl dexamethasone, dexamethasone-phosphate, beclomethasone dipropionates, clobetasol valerate, desonide, desoximetasone, desoxycorticosterone acetate, dexamethasone, dichlorisone, diflorasone diacetate, diflucortolone valerate, fluclorolone acetonide, fludrocortisone, flumethasone pivalate, fluocinolone acetonide, fluocinonide, fluocortolone, fluprednidene acetate, flurandrenolone, halcinonide, hydrocortisone acetate, hydrocortisone butyrate, methylprednisolone, triamcinolone acetonide, cortisone, cortodoxone, fludrocortisone, diflorasone diacetate, fludrocortisone, fluocinolone, medrysone, betamethasone, chloroprednisone, clocortolone, dichlorisone, difluprednate, flunisolide, fluorometholone, hydrocortisone valerate, hydrocortisone, hydrocortamate, paramethasone, prednisolone, prednisone, beclomethasone dipropionate, triamcinolone. Mixtures of the above steroidal anti-inflammatory compounds may also be used.

Non-limiting examples of non-steroidal anti-inflammatory compounds include nabumetone, celecoxib, etodolac, nimesulide, gold, oxicams, such as piroxicam, isoxicam, meloxicam, tenoxicam, sudoxicam, the salicylates, such as aspirin, disalcid, benorylate, trilisate, safapryn, solprin, diflunisal, and fendosal; the acetic acid derivatives, such as diclofenac, fenclofenac, indomethacin, sulindac, tolmetin, isoxepac, furofenac, zidometacin, acemetacin, fentiazac, zomepirac, oxepinac, felbinac, and ketorolac; the fenamates, such as mefenamic, meclofenamic, flufenamic, niflumic, and tolfenamic acids; the propionic acid derivatives, such as ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, and tiaprofenic; and the pyrazoles, such as phenylbutazone, oxyphenbutazone, feprazone, azapropazone, and trimethazone.

In other embodiments, the compounds are administered in combination with medications that prevent indigestion or gastritis such as H2 receptor antagonists (cimetidine, ranitidine, famotidine, and nizatidine) or proton pump inhibitors such as omeprazole, lansoprazole, dexlansoprazole, esomeprazole, pantoprazole, and rabeprazole.

These compounds could be co-administered with analgesics to treat acute or chronic pain conditions. Examples of such analgesics would be opioid agonists (including morphine, codeine, methadone, meperidine, etc.), $\alpha_2$-adrenergic agonists (such as clonidine), gabapentin, and cholinesterase inhibitors (such as donepezil).

Multitargeting Chimeric Antidepressant; a Hybrid of Histone Deacetylase Inhibitor and Serotonin-Norepinephrine Reuptake Inhibitor Through combinatorial synthesis, in vitro, and in vivo screening, a compound (HM3a-R) was identified exhibiting an excellent antidepressant-like activity and fast onset time in our animal models without cellular toxicity, compared with PDX-101 (belinostat), the most potent BBB-permeable HDACI with antidepressant activity.

An increasing number of studies suggest that epigenetic modifications including histone deacetylation occur in the regions of nucleus accumbens, hippocampus, and neural circuits of depressed brains. Accordingly, chromatin-based epigenetic regulation seems to be a promising direction for the development of antidepressant drugs.

Protein acetylation has significant effects on post-translational modifications that regulate multiple cellular functions, including chromatin remodeling, transcriptional regulation, metabolism, and aging. Protein acetylation is regulated by two classes of functionally antagonistic enzymes: protein acetyltransferase and deacetylases. Enzymes that modulate the acetylation of histones as they are major components of chromatin have roles in cellular functions and pathogenesis. Acetylation of lysine residues, catalyzed by acetyltransferases, removes the positive charges of ε-amino groups on lysine residues, relaxes chromatin structure, and increases accessibility for the transcription machinery. Conversely, removal of acetyl groups from histones and other nuclear proteins by histone deacetylases (HDACs) induces chromatin condensation and transcriptional repression. Histone deacetylation can also modulate the function of many other proteins involved in the regulation of cell survival, angiogenesis, inflammation, and immunity.

The superfamily of HDACs has been recognized as an important therapeutic target for cancer treatment and the potential treatment for neuropsychiatric disorders. HDAC contributes to transcriptional activation by relaxing a repressive chromatin state which sequestrates the basal transcriptional machinery associated with depression. Furthermore, expression levels of various HDACs are modulated by antidepressants and mood stabilizers in neuronal and non-neuronal tissue culture systems. Therefore, histone acetylation has emerged as a new target for antidepressant action. Aberrant activity of HDACs has been found in the nucleus accumbens of depressed human brain, leading to development of histone deacetylase inhibitors (HDACIs) as antidepressants. HDACIs enhance histone acetylation, resulting in chromatin relaxation, modulation of gene expression, and reversion of epigenetic changes.

The co-administration of a behaviorally inactive dose of HDACI (ACY-738) and a sub-effective dose of SSRI (citalopram) exerted effects comparable to a 40-fold higher dose of citalopram administered alone (Jochems et al., 2014). Combination treatment regimens are not problem-free due to the increased potential of dangerous drug-drug interactions and the likelihood of unwanted side effects such as epileptic seizure. Moreover, currently available HDACIs are too powerful with marked side effects (fatigue, GI distress, cardiac effects, and hematologic toxicity) to be used as a long-term medication.

In this regard, single molecule that act upon two different molecular targets was developed to create a synergistic combination effect. To achieve this goal, chimeric approach was adopted using the pharmacophores of HDACIs with the scaffolds of SNRIs. A series of cyclopropane derivatives were synthesized. Certain cyclopropyl derivatives were more potent than milnacipran via in vitro assay. Multitargeting chimeric compounds were produced by hybridizing zinc-binding moieties of established HDACIs with SNRI cyclopropyl derivatives.

In Vitro HDACI Activity Test (Western Blot)

The HDACI activity chimeric compounds were tested by western blot using a specific antibody against acetylated histone H4, and 9 L rat glioma cell line. the inhibitory activity of HM3a-R was analyzed at different concentrations (1 μM or 5 μM) on histone H4 deacetylation, compared with established HDACi, entinostat, (pyridin-3-yl)methyl-4-(2-aminophenylcarbamoyl)benzylcarbamate, MS-275 (1 μM or 5 μM) as positive controls. Western blots displayed that both MS-275 and HM3a-R increased histone H4 acetylation at the concentration of 5 μM. Moreover, MS-275 yielded higher inhibitions than HM3a-R consistently at 1 μM and 5 μM.

Xylene-Induced Mouse Ear Edema Test

Randomly selected C57BL adult female mice (6 weeks, ~20 g) were divided into three groups of five mice in per group. Chimeric compounds (HM3a-R, HM3a-S, FIG. 2A) were dissolved in 10% dimethyl sulfoxide and 90% vehicle mixture. Vehicle formulation is 45% (2-hydroxypropyl)-β-cyclodextrin solution. And then, the compounds or vehicle were injected into mice as does 10 mg/kg and injection volume 100 μL intraperitoneally. After 30 min, mice treated 30 μL of xylene on the anterior and posterior surfaces of the right ear lobe, the left ear was considered as control. Two hours later, mice were sacrificed by using $CO_2$ gas and both ears were cut off by using a cork borer with a diameter of 7 mm and weighed and the percentage of ear edema was calculated based on the weight of another ear without xylene.

Figure 3:
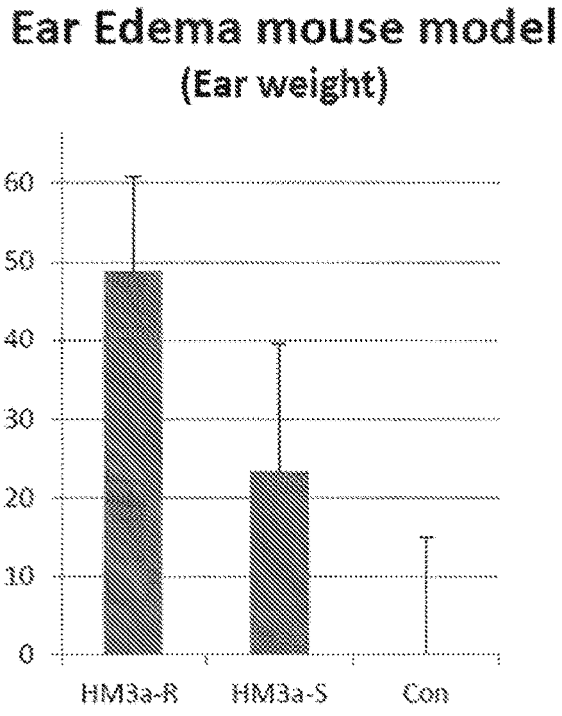
FIG. 3 shows data on xylazine-induced ear inflammation. HM3a-R was more effective than HM3a-S against xylazine-induced ear inflammation. R form was more effective against carrageenan-induced paw edema model as well.

The anti-inflammation activity of multitargeting antidepressant compounds, HM3a-R and HM3a-S, were tested using xylene-induced ear inflammation mouse model, since a number of studies suggested that neuroinflammation often associated with the depression and hydroxamic acids are a class of compound with anti-inflammatory activity. The groups treated with HM3a-R and HM3a-S revealed anti-inflammation effect of 48% and 23% respectively, compared with the control group against xylene-induced ear edema (FIG. 3).

Tail Suspension Test (TST)

Randomly selected NIH Swiss adult male mice (7 weeks, ~30 g) were divided into three groups of 5 mice in per group. LPS (Lipopolysaccharide) was administered as does 850 μg/kg in saline 100 μL intraperitoneally. After 1 h, chimeric compound (HM3a-R, FIG. 2A) or belinostat (Spectrum Pharmaceutical, Irvine, CA) was injected into mice as does 75 mg/kg in vehicle 100 μL intraperitoneally. Then the compounds were dissolved in 10% dimethyl sulfoxide and 90% vehicle mixture. Vehicle formulation is 45% (2-hydroxypropyl)-β-cyclodextrin solution. After 6 h and 24 h, tail suspension test was performed. Every tail-hanged mouse was video-recorded for 6 minutes. And within 6 minutes, the time spent immobile for each mouse was counted by two people who did not know the purpose of the experiment.

Figure 4:
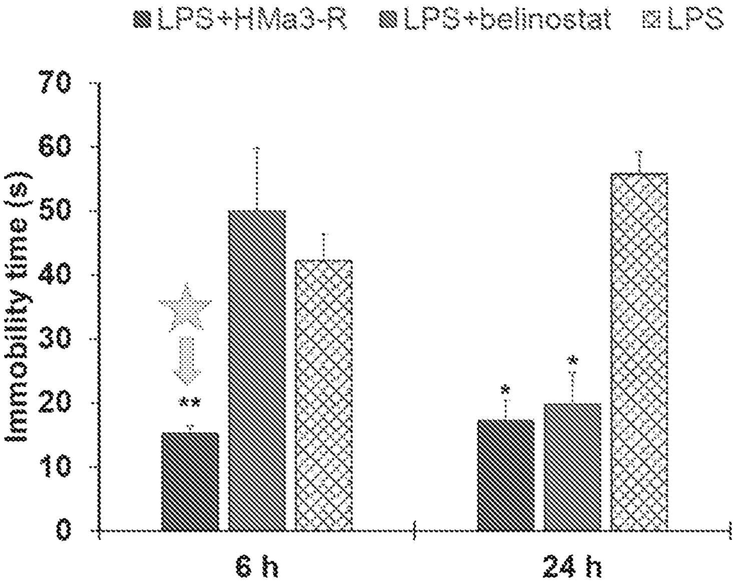
FIG. 4 shows data on the effects of HM3a-R in tail suspension test. Depressed animals are expected to spend increased time in "immobility" than their normal counterparts. Lipopolysaccharide induces depression generating a population that will suffer from enhanced immobility. The inclusion on HM3a-R in the presence of lipopolysaccharide leads a reduction in immobility after 6 and 24 hours.

The tail suspension test (TST) was performed to assess antidepressant-like activity using lipopolysaccharide (LPS) which is an endotoxin that causes depressive behavior in mice. The antidepressant activities of HM3a-R and belinostat were compared with a control. HM3a-R was as effective as belinostat 24 h after LPS injection. More importantly, HM3a-R showed a significantly reduced duration of immobility already 6 h after LPS injection, while belinostat didn't show any effect at that point. Namely, HM3a-R displayed the faster onset of antidepressant action ($P<0.01$, $n=5$) than belinostat (FIG. 4).

Forced Swimming Test (FST)

The FST experiment was performed twice, the first experiment comparing the control group and the HM3a-R group, and the second experiment comparing the control group and the belinostat group. In the first FST, randomly selected C57BL adult female mice (6 weeks, ~20 g) were divided into two groups of eight mice per group. And the second FST, randomly selected C57BL adult female mice (6 weeks, ~20 g) were divided into two groups of five mice per group. Chimeric compounds, HM3a-R (FIG. 2A) was dissolved in 10% dimethyl sulfoxide and 90% vehicle mixture. Vehicle formulation is 45% (2-hydroxypropyl)-β-cyclodextrin solution. Then, HM3a-R or belinostat as dose 75 mg/kg or vehicle (for control) was injected into mice with 100 μL volume intraperitoneally. After 6 h, two 3-liter beakers were filled approximately with 2 L water at 25+/−0.5 degrees Celsius. Camcorder was placed, directly across from two beakers. Each pair of mice (i.e., one control mouse and one treated mouse) was placed into each beaker. Every trial was video recorded in this manner for 10 minutes. While the beakers were adjacent to each other, they were enclosed by cardboard boxes. The immobile times (between 2 and 8 minutes of 10-minute trial) for each pair of mice were counted by the person who was blinded to the identities of the control and treated mice pairs. This was done by taking a stopwatch and summing up the time intervals in which the mice were immobile (i.e., only floating and not actively swimming. “Actively swimming” is defined as using both hind legs in a manner that is more proactive than wading or floating.

Figure 5:
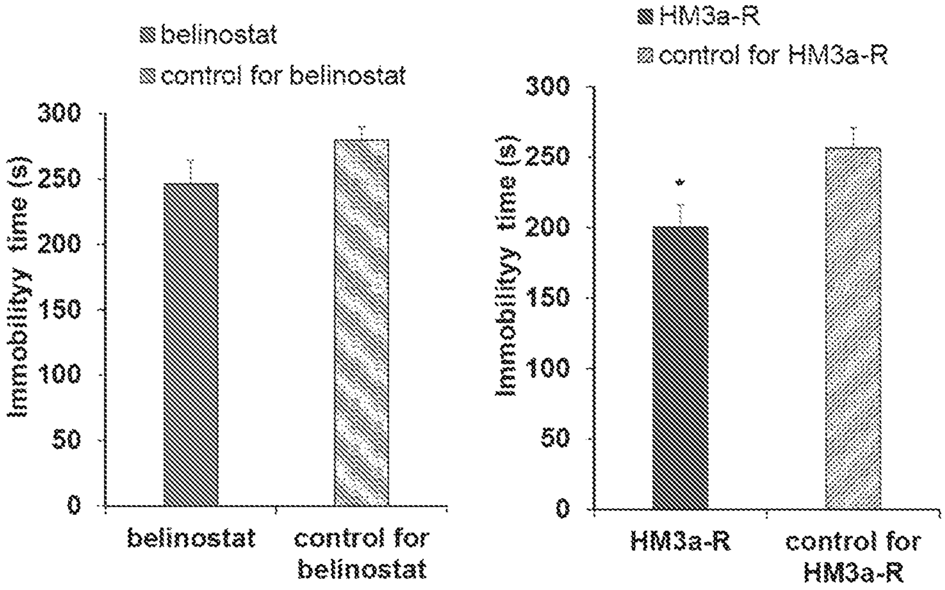
FIG. 5 shows data from a forced-swim test of belinostat left vs. HM3a-R right. HM3a-R shows 23% improvement while belinostat shows only 12%.
Figure 6A:
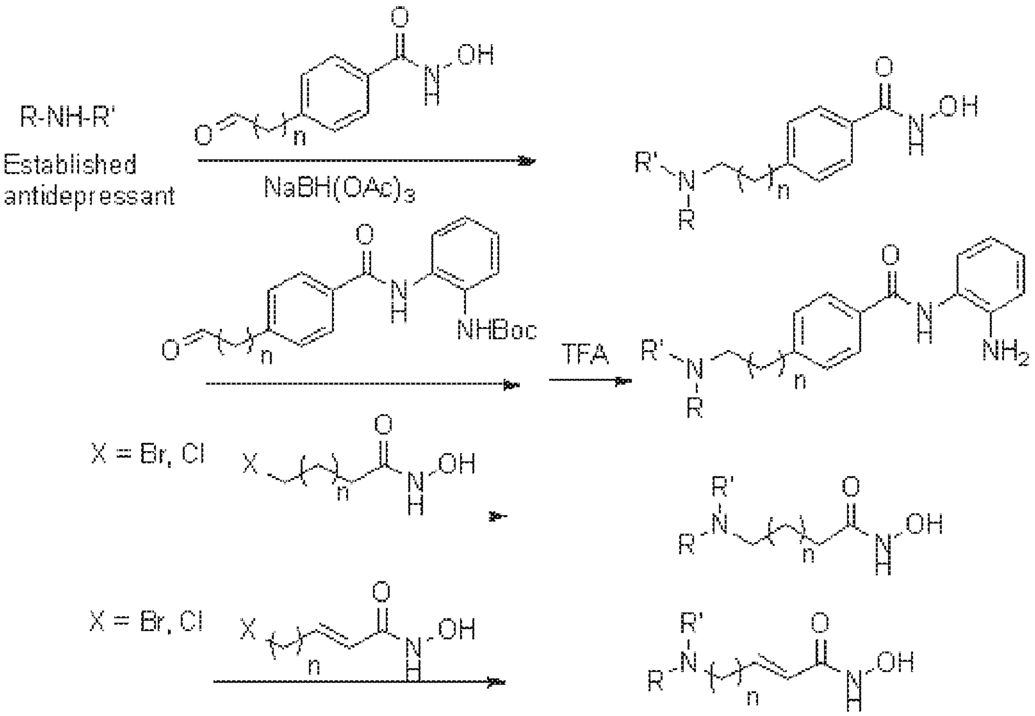
FIG. 6A illustrates the preparation of additional embodiments of this disclosure.
Figure 6B:
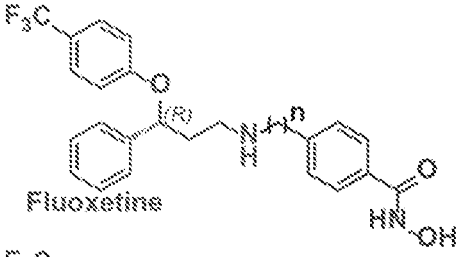
FIG. 6B illustrates additional embodiments of this disclosure wherein n is from 1 to 3 for SSRI-HDACi compounds. For example, a fluoxetine-HDACi compound (R)—N-hydroxy-4-(((3-phenyl-3-(4-(trifluoromethyl)phenoxy)propyl)amino)methyl)benzamide is contemplated (wherein n is 1). A sertraline-HDACi compound 4-(((1S,4S)-4-(3,4-dichlorophenyl)-1,2,3,4-tetrahydronaphthalen-1-yl)(methyl)amino)-N-hydroxybutanamide is contemplated (wherein n is 3).
Figure 6B:
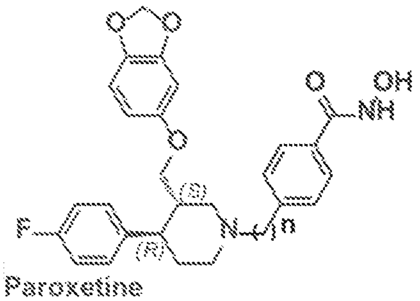
Figure 6B:
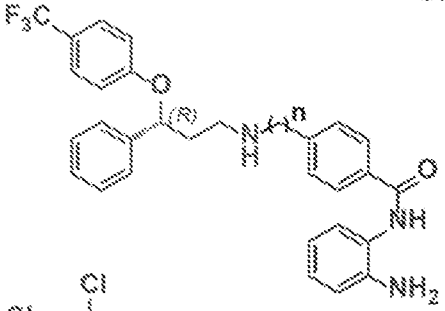
Figure 6B:
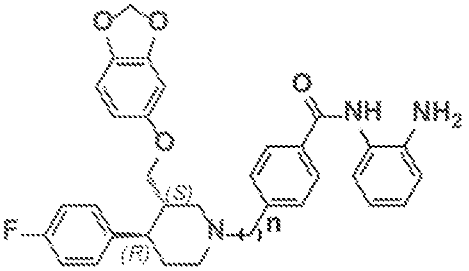
Figure 6B:
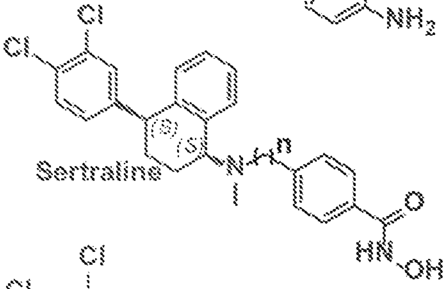
Figure 6B:
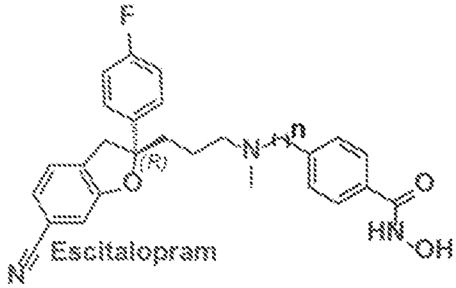
Figure 6B:
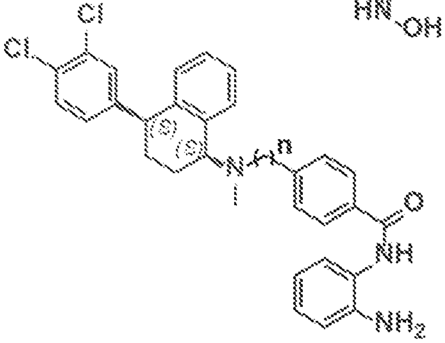
Figure 6B:
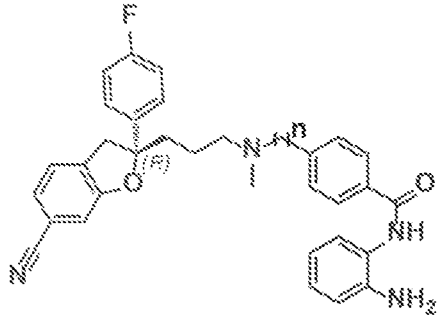
Figure 6C:
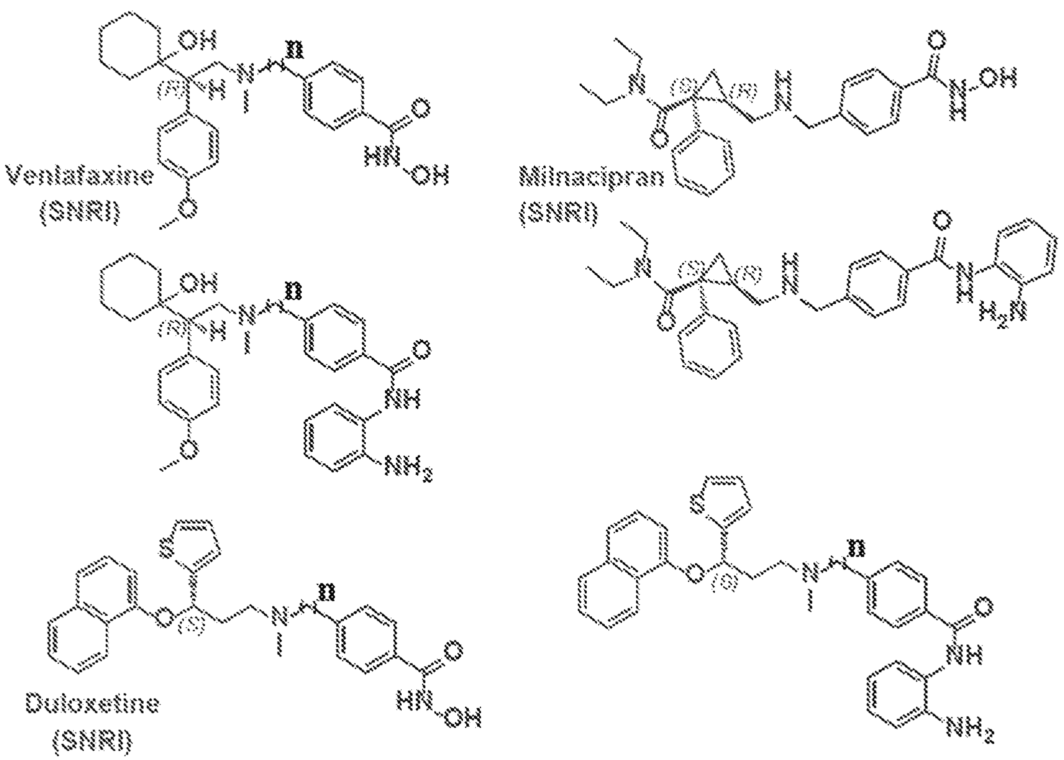
FIG. 6C illustrates additional embodiments of this disclosure wherein n is from 1 to 3 for SNRI-HDACi compounds. For example, an milnacipran-HDACi compound 4-(((((1R,2S)-2-(diethylcarbamoyl)-2-phenylcyclopropyl)methyl)amino)methyl)-N-hydroxybenzamide is contemplated (wherein n is 1). A venlafaxine-HDACi compound (R)—N-hydroxy-4-(((2-(1-hydroxycyclohexyl)-2-(4-methoxyphenyl)ethyl)(methyl)amino)methyl)benzamide is contemplated (wherein n is 1).
Figure 6D:
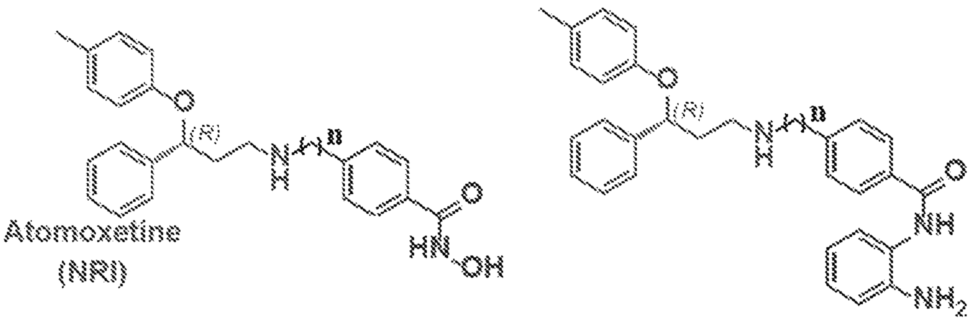
FIG. 6D illustrates additional embodiments of this disclosure wherein n is from 1 to 3. For example, a atomoxetine-HDACi compound (R)—N-hydroxy-4-(((3-phenyl-3-(p-tolyloxy)propyl)amino)methyl)benzamide is contemplated (wherein n is 1).
Figure 7:
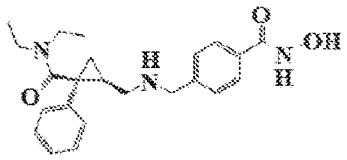
FIG. 7 shows data from a forced swim test using a milnacipran-HDACi compound 4-(((((1R,2S)-2-(diethylcarbamoyl)-2-phenylcyclopropyl)methyl)amino)methyl)-N-hydroxybenzamide (RB-513).
Figure 7:
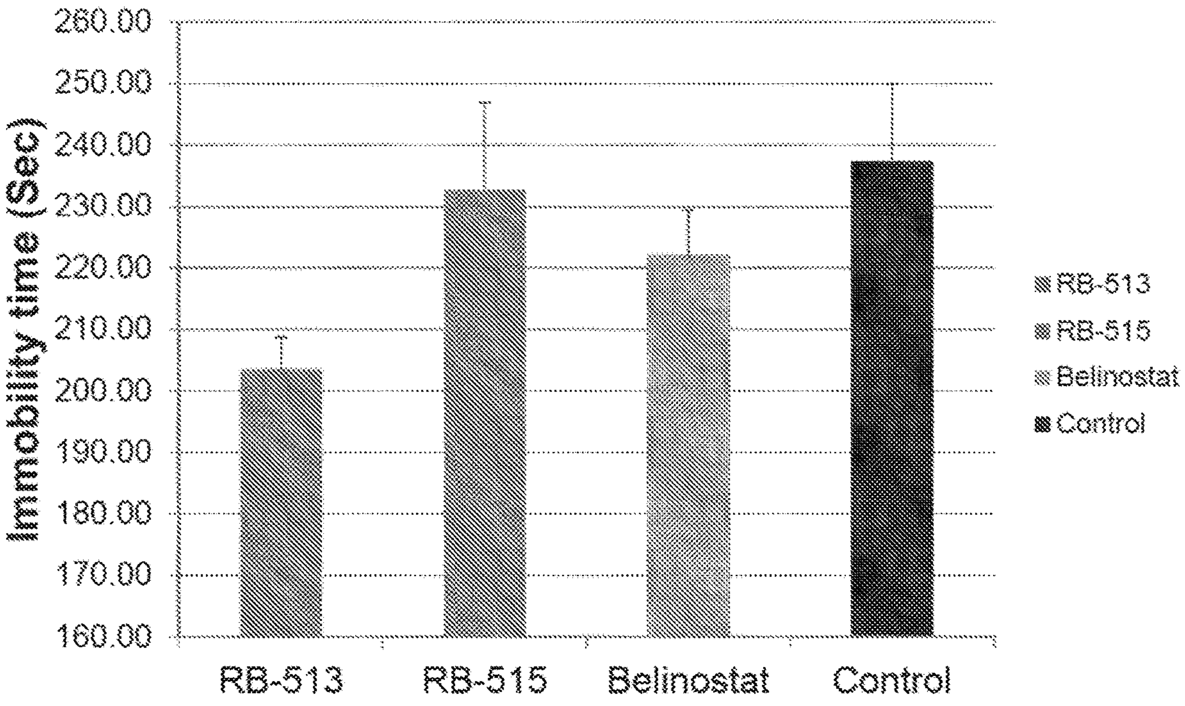

The forced swim test (FST) was conducted as a test for evaluating antidepressant-like activity. In this test, HM3a-R treated mice exhibited significantly less duration of immobility (i.e., more active swimming time) ($P<0.05$, $n=5$). To wit, HM3a-R displayed almost two-fold antidepressant-like activity (23% vs. 12%) than belinostat (FIG. 5).

Compound Preparation

Methods for the preparation of certain cyclopropyl derivatives are disclosed in Pelphrey et al., Chem. Sci., 2010, 1, 254-257, Davies et al., Tetrahedron Letters, (1996) 37(24), 4133-4136, Denton & Davies, Organic Letters, (2009) 11(4), 787-790, Davies & Denton, Chem. Soc. Rev., 2009, 38, 3061-3071 and U.S. Pat. No. 10,207,984. See also U.S. Pat. Nos. 4,567,288, 7,385,064, and U.S. Published Application No. 2008/0051604 and 2014/0045936 all hereby incorporated by reference.

In certain embodiments, the disclosure relates to a process of producing a compound of formula I comprising mixing a reducing agent such as $NaBH_4$ or $Na(OAc)_3BH$, a compound of formula III, V, VII, or VIII, and a compound of formula IV or VI, wherein Formula III

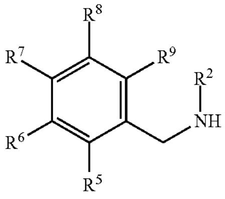

Formula IV

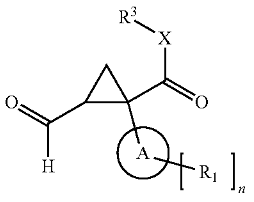

,

Formula V

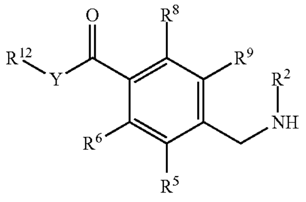

-continued

Formula VI

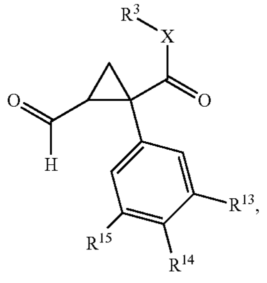

Formula VII

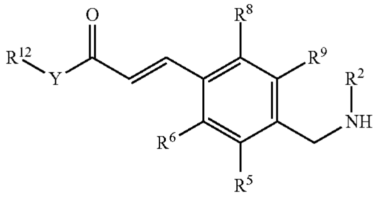

Formula VI

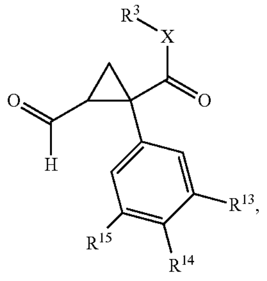

Formula VIII

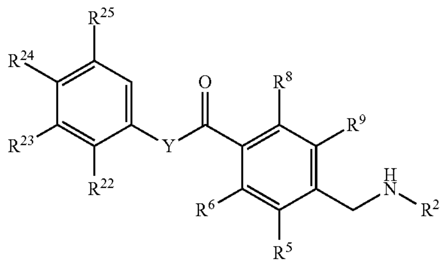

Formula VI

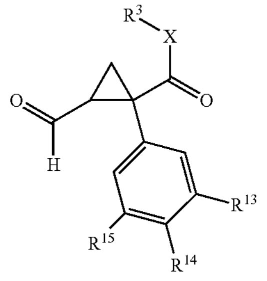

In certain embodiments, the disclosure relates to a process of producing a compound of formula I comprising mixing a reducing agent such as $NaBH_4$ or $Na(OAc)_3BH$, a compound of formula IX, XI, XIII, or XIV, and a compound of formula X or XII, wherein Formula IX

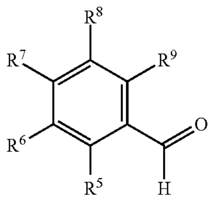

Formula X

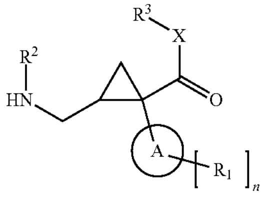

,

Formula XI

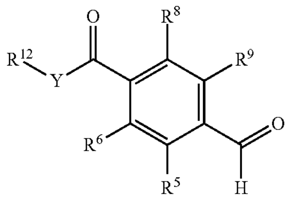

Formula XII

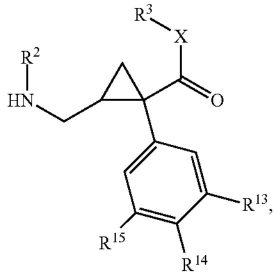

Formula XIII

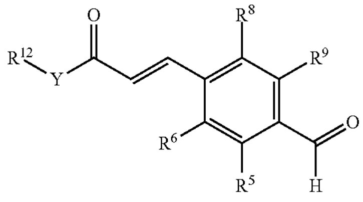

Formula XII

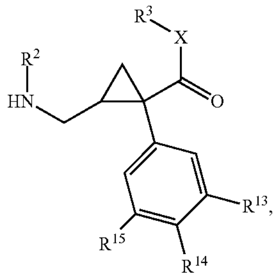

-continued

Formula XIV

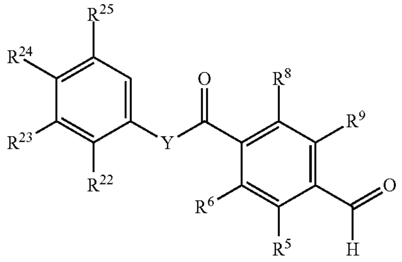

Formula XII

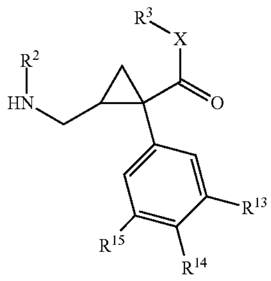

under conditions such that a compound of formula I, IA, IB, or IC is formed.

The synthesis of methyl (1R,2R)-1-(3,4-dichlorophenyl)-2-formylcyclopropane-1-carboxylate (7) and its enantiomer 9 follows the general procedure reported in U.S. Pat. No. 10,207,984:

Synthesis of Dichloro Aryl Diazoacetate

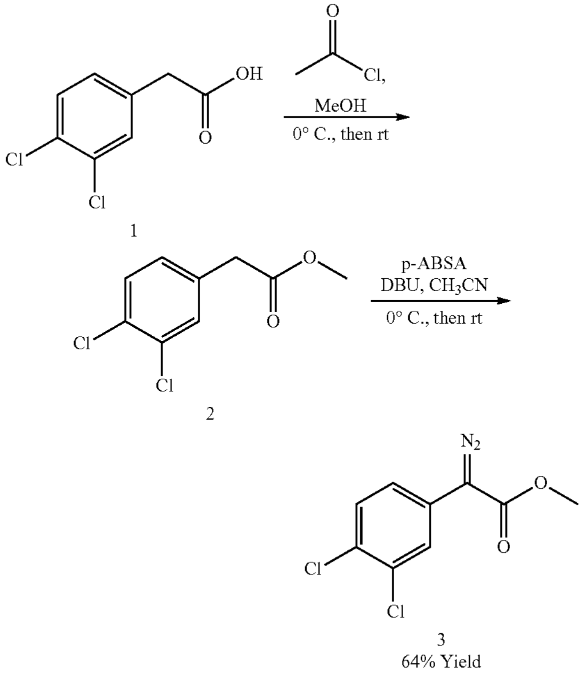

1

2

3

Methyl 2-(3,4-dichlorophenyl)acetate (2): 3,4-dichlorophenylacetic acid (5.4 g, 26.8 mmol) and methanol (50 mL) was added into 100 mL round bottom flask with a stir bar. The reaction flask was cooled down to 0° C., and then acetyl chloride (4.2 g, 53.7 mmol) was added dropwise at 0° C. The reaction was stirred at RT overnight. The reaction mixture was poured into saturated ammonium chloride solution and extracted with diethyl ether (3×40 mL). The combined organic layers were washed with brine, dried over anhydrous $MgSO_4$ and the solvent was removed under reduced pressure. The material was taken on to the next step without further purification. $^1H$ NMR (400 MHz, $CDCl_3$) δ 7.40 (d, J=6.0 Hz, 2H), 7.13 (dd, J=2.0, and 2.0 Hz, 1H), 3.71 (s, 3H), 3.59 (s, 2H).

Methyl 2-diazo-2-(3,4-dichlorophenyl)acetate (3): 2 and p-acetamidobenzenesulfonyl azide (p-ABSA) (7.3 g, 30.4 mmol) were dissolved in acetonitrile (20 mL) and cooled to 0° C. 1,8-Diazabicyclo-[5,4,0]-undec-7-ene (DBU) (7.4 g, 48.7 mmol) in acetonitrile (10 mL) was added dropwise at 0° C., and the reaction was stirred at RT overnight. The reaction mixture was poured into saturated ammonium chloride solution and extracted with diethyl ether (2×100 mL). The combined organic layers were washed with brine and dried over anhydrous $MgSO_4$. The solvent was removed under reduced pressure. The product was purified by flash chromatography (silica gel, 3:1 hexane:diethyl ether) to obtain an orange solid (4.8 g, 64% yield). $^1H$ NMR (400 MHz, $CDCl_3$) δ 7.65 (d, J=2.4 Hz, 1H), 7.44 (d, J=8.4 Hz, 1H), 7.29 (dd, J=2.0, and 2.4 Hz, 1H), 3.88 (s, 3H).

Synthesis of (E)-Buta-1,3-dienylbenzene

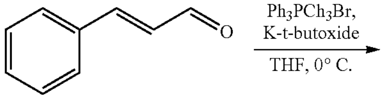

4

-continued

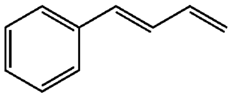

5

57% Yield (E)-Buta-1,3-dienylbenzene (5): Methyltriphenylphosphine bromide (17.9 g, 50 mmol) and THF (100 mL) was added into 500 mL round bottom flask with a stir bar. The reaction flask was cooled down to 0° C., and then potassium tert-butoxide (8.4 g, 75 mmol) was added. The reaction was stirred for 5 h at 0° C. under an atmosphere of argon. (E)-3-phenylacrylaldehyde 4 (6.6 g, 170 mmol) in THF (14 mL) was added dropwise over 1 h, and the reaction was stirred overnight. The reaction mixture was poured into $H_2O$ (200 mL) and extracted into pentane (3×40 mL). The combined organic layers were washed with brine, dried over anhydrous $MgSO_4$. Hexane (100 mL) was added to the combined organic layers to precipitate triphenyl phosphine oxide. The reaction mixture was filtered through silica gel and the solvent was removed under reduced pressure. The product was purified by Kugel Rohr distillation (85° C.) to obtain a colorless liquid (3.5 g, 54% yield). $^1H$ NMR (400 MHz, $CDCl_3$) δ 7.41 (d, J=7.2 Hz, 2H), 7.31 (t, 2H), 7.22 (t, 1H), 6.78 (dd, J=10.4, and 10.4 Hz, 1H), 6.60-6.48 (m, 2H), 5.34 (d, J=17.2 Hz, 1H), 5.18 (d, J=10.0 Hz, 1H).

Synthesis of Enantiomers of Arylcyclopropylaldehyde Compounds

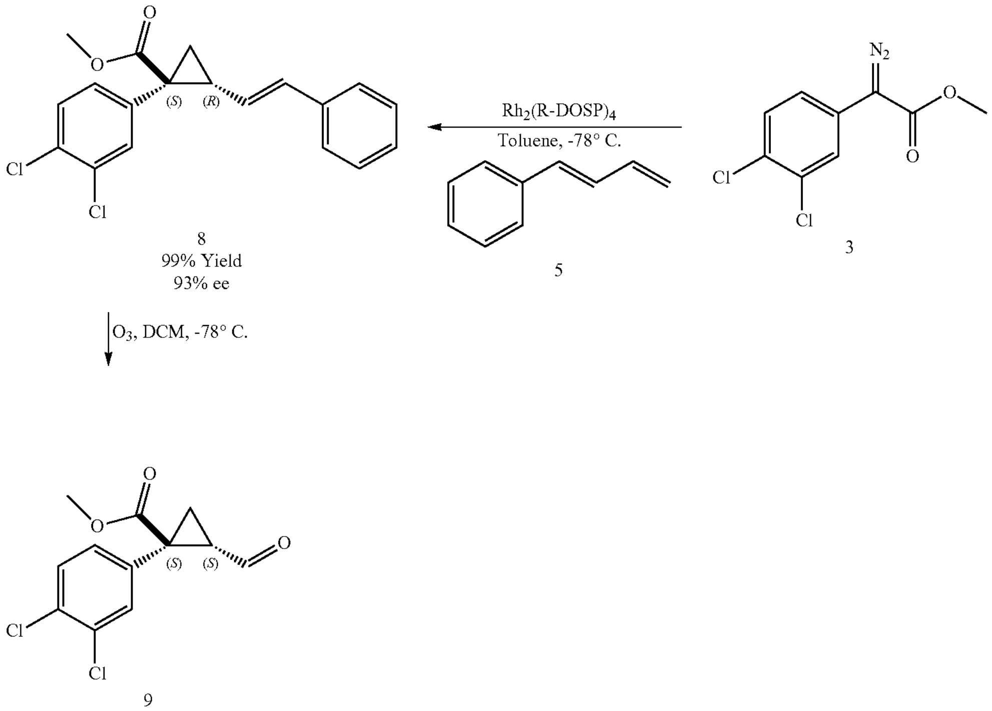

-continued

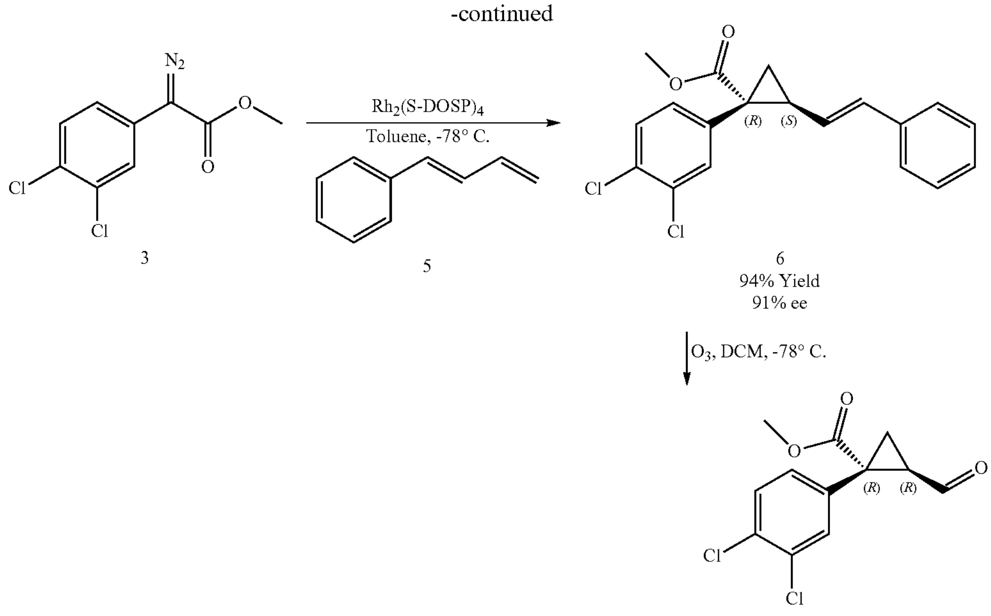

3

5

6
94% Yield
91% ee 7
99% Yield

Methyl (1R,2S)-1-(3,4-dichlorophenyl)-2-((E)-styryl)cyclopropane-1-carboxylate (6): To an oven dried 100 mL round bottom flask with a stir bar was added (E)-buta-1,3-dienylbenzene 5 (781 mg, 6 mmol), Rh$_2$(S-DOSP)$_4$ (28 mg, 1% mol), and dry, degassed toluene (4 mL). The reaction vessel was cooled to −78° C. in a dry ice and acetone bath. The diazo compound 3 (490 mg, 2 mmol) was dissolved in dry, degassed toluene (20 mL) and added by syringe pump over 2 h at −78° C. under an atmosphere of argon. The reaction was stirred and allowed to warm to room temperature overnight. The solvent was removed under reduced pressure and the product was purified by flash chromatography (silica gel, 8:1 hexane:ethyl acetate) to obtain 94% yield (654.2 mg). HPLC analysis: 91% ee (OD-H column, 1% 2-propanol in hexane, 1.0 mL/min, $t_R$=6.58 (major) and 9.77 (minor) min); $^1$H NMR (400 MHz, $CDCl_3$) δ 7.42-7.38 (m, 2H), 7.26-7.12 (m, 6H), 6.61 (d, J=15.6 Hz, 1H), 5.19 (dd, J=9.6, and 9.6 Hz, 1H), 3.66 (s, 3H), 2.73-2.67 (m, 1H), 2.06 (dd, J=9.2, and 9.2 Hz, 1H), 1.44 (dd, J=4.8, and 4.8 Hz, 1H).

Synthesis of the enantiomer of Methyl (1S,2R)-1-(3,4-dichlorophenyl)-2-((E)-styryl)cyclopropane-1-carboxylate (8) was carried out using Rh$_2$(R-DOSP)$_4$ (1% mol) as catalyst in the same reaction conditions as described above to obtain 99% yield. HPLC analysis: 93% ee (OD-H column, 1% 2-propanol in hexane, 1.0 mL/min, $t_R$=6.01 (minor) and 8.24 (major) min). NMR spectroscopic data is same as 6.

Methyl (1R,2R)-1-(3,4-dichlorophenyl)-2-formylcyclopropane-1-carboxylate (7): In a 100 mL round bottom flask with a stir bar, 6 (345.7 mg, 1 mmol) was dissolved in dichloromethane (20 mL) and flushed with argon. This solution was then cooled to −78° C. through an acetone and dry ice bath. Ozone was bubbled through the solution until a blue color persisted, and then oxygen was bubbled through the solution for 5 min. Triphenylphosphine (262.3 mg, 1 mmol) was added to quench the reaction and stirred overnight while warming to room temperature. The reaction mixture was concentrated under reduced pressure and purified by flash chromatography (silica gel, 8:1 hexane:ethyl acetate) to give the product as a colorless oil (268 mg, 99% yield). $^1$H NMR (400 MHz, $CDCl_3$) δ 8.76 (d, J=5.6 Hz, 1H), 7.44-7.41 (m, 2H), 7.13 (dd, J=2.4, and 2.0 Hz, 1H), 3.69 (s, 3H), 2.84-2.78 (m, 1H), 2.15 (dd, J=4.8, and 4.8 Hz, 1H), 2.09-2.05 (m, 1H).

Synthesis of the enantiomer of 9 was carried out using 8 as starting material in the same reaction conditions as described above to obtain in 93% yield of product. NMR spectroscopic data of 9 is same as 7.

Synthesis of Methylamine Intermediate with Benzyl Ester

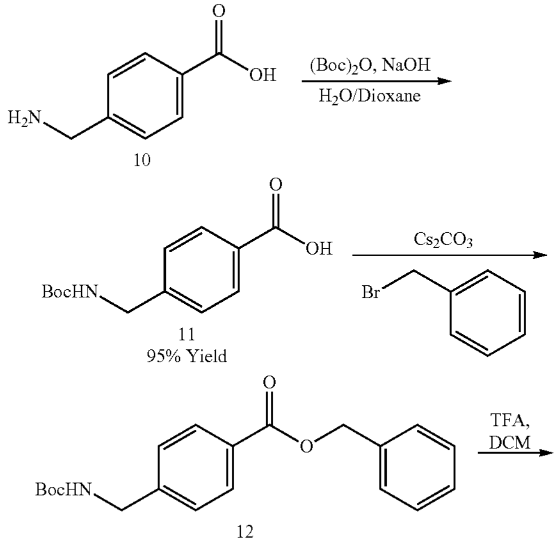

10

11
95% Yield 12
80% Yield

-continued

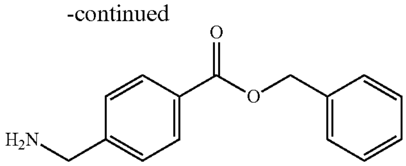

13

4-(((tert-Butoxycarbonyl)amino)methyl)benzoic acid (11): 4-(Aminomethyl)benzoic acid (2.0 g, 13.1 mmol, 1 eq) was dissolved in dioxane (32 mL) and water (16 mL) at RT. 1M NaOH (aq) (16 mL, 15.7 mmol, 1.2 eq) was added and the solution was cooled to 4° C. in an ice bath. Di-tert-butyl dicarbonate (3.1 g, 14.4 mmol, 1.1 eq) was added and the solution was allowed to warm slowly to room temperature. After 15 hours, the dioxane was removed under reduced pressure. The remaining aqueous solution was acidified to pH 2 with 10% $KHSO_4$ (aq) and extracted with EA. The organic layer was dried over $Na_2SO_4$, filtered and condensed to give 11 as a white solid (3.2 g, 95%). $^1$H NMR (400 MHz, DMSO) δ 7.89 (d, J=8.4 Hz, 2H), 7.48 (t, 1H), 7.33 (d, J=8.0 Hz, 2H), 4.18 (d, J=6.4 Hz, 2H), 1.39 (s, 9H).

A mixture of 11 (2.7 g, 10.5 mmol, 1.0 eq), benzyl bromide (1.8 g, 10.5 mmol, 1.0 eq) and $Cs_2CO_3$ (3.8 g, 11.6 mmol, 1.1 eq) in DMF (20 mL) was stirred at RT for 1 h. Then the solution was poured into water (20 mL), extracted with ethyl acetate (30 mL×2), and dried over $MgSO_4$. The organic layer was concentrated to give the crude product, which was further purified by column chromatography ($SiO_2$, Hexane:Ethyl acetate=4:1) to give 12 as a white powder (2.9 g, 81%). mp 74~77° C.; IR (neat) ν (cm-1) 3362, 2976, 1694, 1507, 1366, 1267, 1164, 1099, 752, 696; $^1$H NMR (400 MHz, $CDCl_3$) δ 8.05 (d, J=8.4 Hz, 2H), 7.47-7.34 (m, 7H), 5.37 (s, 2H), 4.37 (d, J=6.0 Hz, 2H), 1.47 (s, 9H); $^{13}$C NMR (100 MHz, CDCl3) δ 166.4, 156.1, 144.6, 136.2, 130.2, 129.3, 128.8, 128.4, 127.4, 80.0, 66.9, 64.5, 44.5, 28.6; HRMS (ESI): m/z calcd for $C_{20}H_{23}NO_4Na^+$ ($M+Na^+$): 364.1525, found: 364.1528.

Trifluoroacetic acid (6.4 mL, 83.0 mmol) was added dropwise to a stirred solution of 12 (2.8 g, 8.3 mmol) in $CH_2Cl_2$ (20 mL). The mixture was stirred at RT for 2 h. evaporated to dryness under reduced pressure, and co-evaporated twice with absolute EtOH (100 mL×2) to afford 13 as a light yellow solid (quantitative). mp 115~117° C.; IR (neat) ν ($cm^{-1}$) 3427, 2891, 1670, 1273, 1200, 1182, 1130, 722; $^1$H NMR (400 MHz, DMSO) δ 8.28 (s, 2H), 8.03 (d, J=8.4 Hz, 2H), 7.59 (d, J=8.4 Hz, 2H), 7.49-7.34 (m, 5H), 5.36 (s, 2H), 4.14 (d, J=5.6 Hz, 2H); $^{13}$C NMR (100 MHz, DMSO) δ 166.3, 139.5, 136.1, 129.6, 129.5, 129.2, 128.6, 128.2, 128.0, 66.4, 41.9; HRMS (ESI): m/z calcd for $C_{15}H_{16}NO_2^+$ ($M+H^+$): 242.1181, found: 242.1199.

Synthesis of Secondary Amine Intermediate

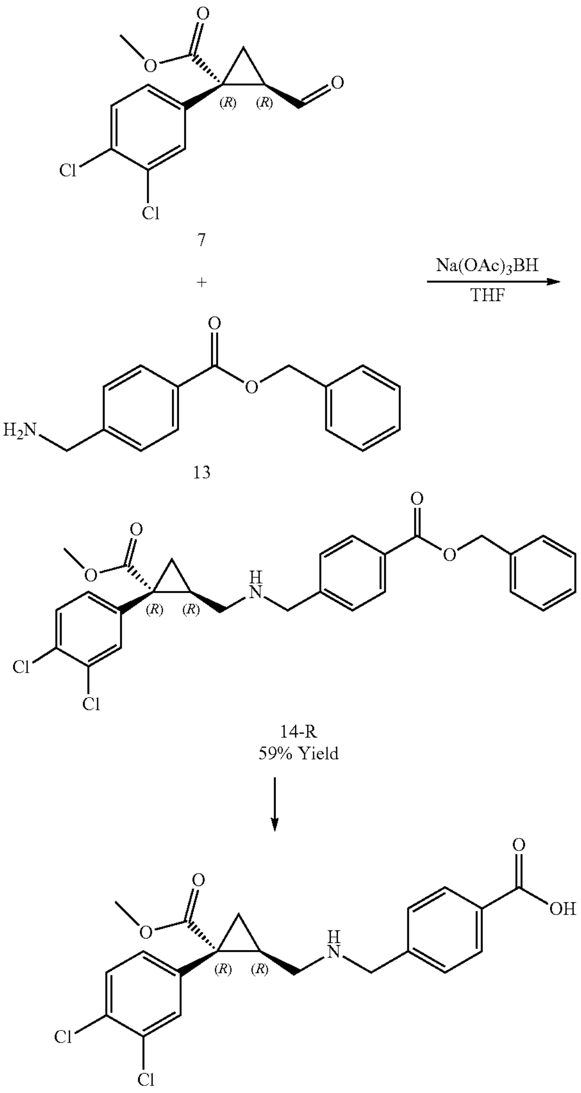

15-R

In a 100 mL round bottom flask equipped with a magnetic stir bar, 7 (73.7 mg, 0.27 mmol, 1 eq.) was dissolved in THF (5 mL) and flushed with argon. This solution was treated with 13 (130.3 mg, 0.54 mmol in 5 mL THF, 2 eq.) and $Na(OAc)_3BH$ (86.9 mg, 0.41 mmol, 1.5 eq) and stirred at RT for 3 h under argon. After the allotted time had passed, the reaction was quenched with aqueous saturated $NaHCO_3$, and the product was extracted with ethyl acetate. The ethyl acetate extract was dried over $MgSO_4$, the organic phase was then filtered and concentrated under reduced pressure and the resulting residue was purified by column chromatography ($SiO_2$, ethyl acetate:Hexane=4:1) to give 14R as a colorless oil in 59% yield (77.9 mg). IR (neat) ν ($cm^{-1}$) 3317, 3032, 2950, 2822, 1714, 1474, 1378, 1267, 1173, 1097, 1030, 908, 752, 728, 696; $^1$H NMR (400 MHz, $CDCl_3$): δ 8.01 (d, J=8.4 Hz, 2H), 7.48-7.35 (m, 7H), 7.28 (d, J=8.4 Hz, 2H), 7.15 (dd, J=2.0, 2.4 Hz, 1H), 5.37 (s, 2H), 3.78 (d, J=13.6 Hz, 1H), 3.67 (d, J=14.0 Hz, 1H), 3.63 (s, 3H), 2.27 (d, J=6.8 Hz, 2H), 2.11-2.04 (m, 1H), 1.74 (dd, J=4.4, 4.4 Hz, 1H), 1.17 (dd, J=6.8, 6.8 Hz, 1H); $^{13}$C NMR (100 MHz, $CDCl_3$) δ 173.8, 166.5, 145.5, 136.3, 136.1, 133.2, 132.2, 131.7, 130.7, 130.2, 130.0, 129.1, 128.8, 128.4, 128.3, 128.0, 66.8, 53.7, 52.8, 49.5, 33.0, 28.6, 20.2; HRMS (ESI): m/z calcd for $C_{27}H_{26}Cl_2NO_4^+$ (M+H$^+$): 498.1239, found: 498.1241.

A mixture of 14-R (167.8 mg, 0.34 mmol, 1 eq) and Pd/C (10% wt, 3.6 mg, 0.034 mmol, 0.1 eq.) were dissolved in MeOH (30 mL). The solution was deoxygenated by purging with Ar for 10 min, and then this solution was hydrogenated at RT, and the progress of the reaction was monitored by TLC (Hex:Ethyl Acetate=1:8). The solid residues were removed by filtration over celite and washed with MeOH. After filtration, the organic layer was evaporated to dryness to give the corresponding acids. Concentration in vacuo gave crude product, which was further purified by column chromatography ($SiO_2$, DCM:MeOH=4:1) to obtain 15-R as a white powder (116.5 mg, 85%). mp 161-165° C.; IR (neat) ν (cm$^{-1}$) 2915, 2629, 1669, 1531, 1194, 1137, 724; $^1$H NMR (400 MHz, $CD_3OD$) δ 7.98 (d, J=8.4 Hz, 2H), 7.57 (d, J=2.4 Hz, 1H), 7.52 (d, J=8.4 Hz, 1H), 7.47 (d, J=8.4 Hz, 2H), 7.29 (dd, J=2.4, 2.0 Hz, 1H), 4.16 (d, J=4.4 Hz, 2H), 3.66 (s, 3H), 2.28-2.21 (m, 1H), 2.18-2.12 (m, 2H), 1.85 (dd, J=5.2, 5.2 Hz, 2H), 1.59 (dd, J=6.8, 6.8 Hz, 1H). $^{13}$C NMR (100 MHz, $CD_3OD$) δ 174.3, 141.5, 138.5, 136.8, 136.2, 134.5, 133.4, 133.1, 132.3, 131.7, 131.1, 130.5, 53.5, 52.3, 49.7, 34.2, 24.5, 21.5; LC-MS: m/z calcd for $C_{20}H_{20}Cl_2NO_4$ (M+H$^+$): 408.1, found: 408.1; HRMS (ESI): m/z calcd for $C_{20}H_{20}Cl_2NO_4$ (M+H$^+$): 408.0769, found: 408.0763.

Synthesis of the (S)(S)-enantiomer, 14-S, was carried out using 9 as starting material in the same reaction conditions as described above to obtain in 59% yield of product. NMR spectroscopic data of 14-S is same as 14-R. Synthesis of the enantiomer of 15-S was carried out using 14-S as starting material in the same reaction conditions as described above to obtain in 84% yield of product. NMR spectroscopic data is same as 15-R.

Synthesis with 2-Aminobenzamide Group

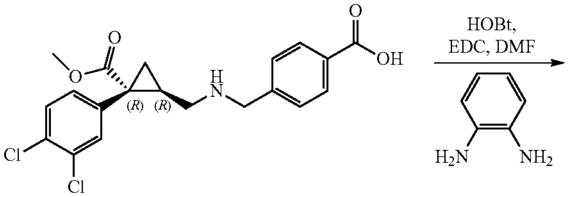

15-R

-continued

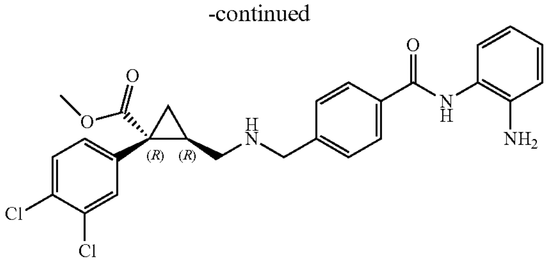

16-R
39% Yield

To a solution of 1,2-phenylenediamine (75.7 mg, 0.7 mmol, 2 eq.) in DMF (3 mL) was added 15-R (144.3 mg, 0.35 mmol, 1 eq.), then 1-hydroxybenzotriazole (HOBt, 71.6 mg, 0.53 mmol, 1.5 eq.) and finally 1-(3-dimethylamino-propyl)3-ethylcarbodiimide hydrochloride (EDC or WSC, 101.6 mg, 0.53 mmol, 1.5 eq.), and the mixture stirred at room temperature for 14 hrs. The reaction mixture was diluted with EtOAc (50 mL), washed with saturated $NaHCO_3$ (50 mL) and brine (50 mL), dried over $MgSO_4$, and concentrated. This filtered yellow solution was purified by column chromatography ($SiO_2$, ethyl acetate 100%; Biotage Isolera). The crude product was purified by preparative TLC on silica gel ($SiO_2$, EA:MeOH=4:1), affording 16-R (68.5 mg, 39%). mp 146-148° C.; $[\alpha]_D^{20}$=−13.4° (C 0.41, $CHCl_3$); IR (neat) ν (cm$^{-1}$) 3288, 2924, 1719, 1651, 1605, 1522, 1453, 1318, 1273, 748; $^1$H NMR (400 MHz, $CD_3OD$): δ 8.10 (d, J=8.4 Hz, 2H), 7.65 (d, J=8.0 Hz, 2H), 7.57 (d, J=1.6 Hz, 1H), 7.40-7.34 (m, 2H), 7.23-7.17 (m, 2H), 6.76 (t, 1H), 6.68 (d, J=8.0 Hz, 2H), 4.20 (s, 2H), 3.62 (s, 3H), 2.59-2.45 (m, 1H), 2.14-2.03 (m, 1H), 1.74 (dd, J=4.4, 4.4 Hz, 1H), 1.41 (dd, J=4.8, 4.8 Hz, 1H). $^{13}$C NMR (100 MHz, $CD_3OD$) δ 175.1, 168.6, 143.9, 139.2, 137.8, 135.8, 134.5, 133.0, 132.6, 132.3, 130.8, 129.9, 129.2, 128.7, 127.8, 125.4, 119.8, 118.9, 53.7, 53.2, 50.1, 34.1, 28.3, 21.1; LC-MS: m/z calcd for $C_{26}H_{26}Cl_2N_3O_3$ (M+H$^+$): 498.1, found: 498.1; HRMS (ESI): m/z calcd for $C_{26}H_{26}Cl_2N_3O_3$ (M+H$^+$): 498.1351, found: 498.1344.

Synthesis of the (S)(S)-enantiomer 16-S was carried out using 15-S as starting material in the same reaction conditions as described above to obtain in 39% yield of product. NMR spectroscopic data is same as 16-R.

Synthesis with Hydroxamic Acid Group, HM3a-S; HM3a-R

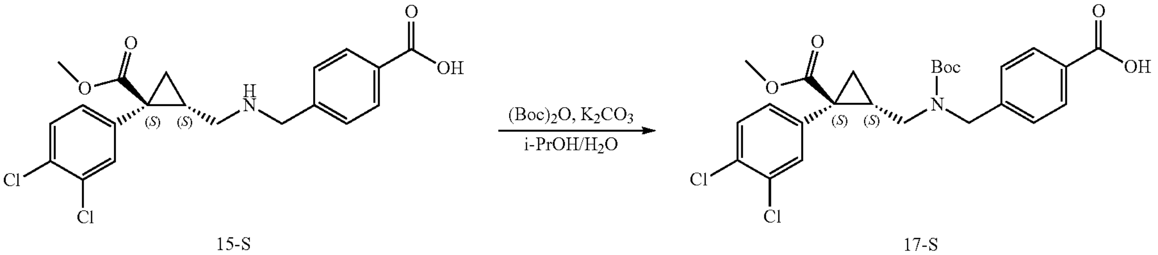

15-S

17-S
99% Yield

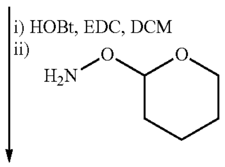

-continued

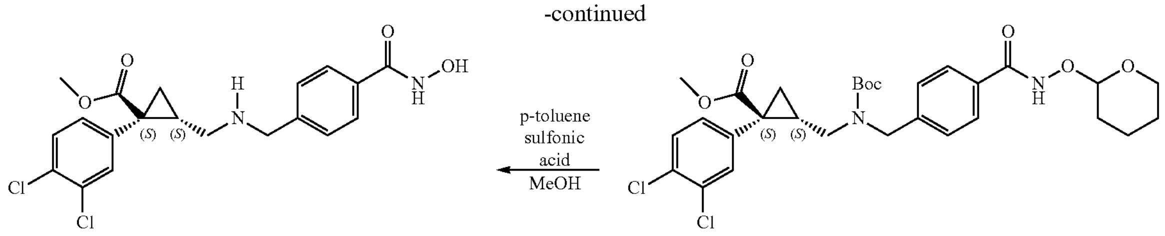

19-S
53% Yield

18-S
89% Yield

15-S (87.0 mg, 0.21 mmol, 1 eq.) was dissolved in i-propanol (3 mL) and water (3 mL) at RT. $K_2CO_3$ (31.8 mg, 0.231 mmol, 1.1 eq.) and di-tert-butyl dicarbonate (59.6 mg, 0.273 mmol, 1.3 eq.) were added and the solution was stirred for 17 h at RT. After 17 hours, the reaction mixture was concentrated under reduced pressure. This was dissolved in ethyl acetate (10 mL), washed with 2N HCl (5 mL), and dried over $Na_2SO_4$. The organic layer was filtered and condensed to give 17-S as colorless oil (105.7 mg, 99%). IR (neat) ν ($cm^{-1}$) 2977, 1722, 1691, 1476, 1411, 1249, 1170, 733; $^1H$ NMR (400 MHz, $CDCl_3$) δ 8.06 (d, J=8.0 Hz, 2H), 7.37-7.21 (m, 4H), 7.09-7.03 (m, 1H), 4.60-4.36 (m, 2H), 3.61 (s, 3H), 2.47-2.37 (m, 1H), 2.10-2.07 (m, 2H), 1.72-1.65 (m, 1H), 1.40 (s, 9H), 1.29-1.26 (m, 1H); $^{13}C$ NMR (100 MHz, $CD_3OD$) δ 173.5, 171.5, 155.7, 135.6, 133.1, 132.5, 132.0, 131.2, 130.7, 130.4, 129.6, 128.4, 128.0, 80.8, 52.9, 52.8, 52.7, 28.5, 26.4, 21.2, 14.4; HRMS (ESI): m/z calcd for $C_{25}H_{26}Cl_2NO_6$ ($M-H^+$): 506.1137, found: 506.1148.

EDC (77.6 mg, 0.41 mmol, 1.5 eq.) and HOBt (47.4 mg, 0.35 mmol, 1.3 eq.) were added to a solution of 17-S (139.4 mg, 0.27 mmol, 1.0 eq.) in $CH_2Cl_2$ (15 ml). The reaction mixture was stirred for 1 hr at room temperature and then $NH_2OTHP$ (79.1 mg, 0.68 mmol, 2.5 eq.) was added. The solution was maintained for 8 h at 50° C. $NaHCO_3$ (1N) was added and the solution was extracted ethyl acetate and brine. The organic layer was dried over $Na_2SO_4$, filtered and concentrated. The resulting crude material was purified by column chromatography (Hex:Etheyl Acetate 3:2) to give 18-S as a white powder (147 mg, 89%). mp 70~73° C.; IR (neat) ν ($cm^{-1}$) 3239, 2948, 1723, 1614, 1475, 1248, 1166, 1150, 1033, 905, 730; $^1H$ NMR (400 MHz, $CDCl_3$) δ 8.94 (s, 1H), 7.70 (d, J=8.0 Hz, 2H), 7.36 (d, J=8.4 Hz, 1H), 7.29-7.28 (m, 1H), 7.20 (d, J=8.0 Hz, 2H), 7.05-7.02 (m, 1H), 5.07 (s, 2H), 4.70-4.23 (m, 2H), 3.99 (t, 1H), 3.64-3.49 (m, 1H), 3.60 (s, 3H), 2.40-2.34 (m, 1H), 2.09-2.07 (m, 1H), 1.88-1.81 (m, 3H), 1.75-1.73 (m, 1H), 1.65-1.58 (m, 4H), 1.39 (s, 9H); $^{13}C$ NMR (100 MHz, $CDCl_3$) δ 173.5, 155.7, 154.3, 135.6, 135.1, 133.1, 132.5, 132.0, 131.2, 130.6, 130.4, 127.7, 127.1, 102.9, 80.7, 62.9, 60.6, 52.9, 52.8, 29.5, 28.5, 28.3, 26.4, 25.2, 18.8, 14.4; HRMS (ESI): m/z calcd for $C_{30}H_{37}Cl_2N_2O_7$ ($M+H^+$): 607.1978, found: 607.1980.

p-Toluenesulfonic acid (32.3 mg, 0.17 mmol, 1.0 eq.) was added to a solution of 18-S (100.8 mg, 0.17 mmol, 1.0 eq.) in MeOH (20 mL). The solution was stirred for 17 h at 80° C. The reaction mixture was monitored by TLC (Eluent: Hex:Ethyl Acetate=3:2). The reaction mixture was concentrated, extracted with saturated $NaHCO_3$ (50 mL) and ethyl acetate (50 mL×2). The organic layer was dried over $Na_2SO_4$, filtered and condensed. The crude product was purified by preparative TLC on silica gel ($SiO_2$, EA:MeOH=4:1), affording 19-S (HM3a-S, 37.0 mg, 53%). $[\alpha]_D^{20}$=+1.6° (C 1.00, $CHCl_3$); IR (neat) ν ($cm^{-1}$) 3246, 2923, 2851, 1717, 1614, 1557, 1474, 1434, 1271, 1031, 898; $^1H$ NMR (400 MHz, $CD_3OD$) δ 7.71-7.68 (m, 2H), 7.51 (s, 1H), 7.42-7.41 (m, 1H), 7.30-7.27 (m, 3H), 3.72-3.69 (m, 2H), 3.61 (s, 3H), 2.42-2.40 (m, 1H), 2.08-2.06 (m, 2H), 1.71-1.70 (m, 1H), 1.35-1.31 (m, 1H); $^{13}C$ NMR (100 MHz, $CD_3OD$) δ 175.3, 167.8, 144.4, 137.9, 134.5, 133.0, 132.5, 132.3, 131.3, 129.6, 128.9, 128.2, 54.1, 53.2, 50.3, 29.7, 28.9, 21.1; HRMS (ESI): m/z calcd for $C_{20}H_{21}Cl_2N_2O_4$ ($M+H^+$): 423.0878, found: 423.0874.

Synthesis of the (R)(R)-enantiomer of 17-R was carried out using 15-R as starting material in the same reaction conditions as described above to obtain in 99% yield of product. NMR spectroscopic data of 17-R is the same as 17-S. Synthesis of the enantiomer of 18-R was carried out using 17-R as starting material in the same reaction conditions as described above to obtain in 93% yield of product. NMR spectroscopic data is same as 18-S. Synthesis of the enantiomer of 19-R (HM3a-R) was carried out using 18-R as starting material in the same reaction conditions as described above to obtain in 54% yield of product. NMR spectroscopic data is same as 19-S.

What is claimed is:

1. A compound having formula IA

Formula I

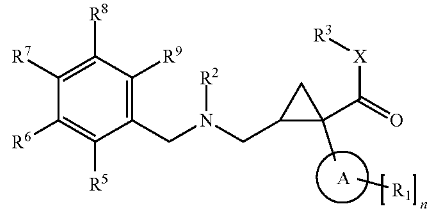

or salt thereof wherein,

X is O or $NR^4$,

Y is $NR^4$;

$R^2$ is hydrogen or $C_{1-4}$alkyl;

$R^3$ is hydrogen or $C_{1-4}$alkyl;

$R^4$ is hydrogen or $C_{1-4}$alkyl;

$R^5$, $R^6$, $R^8$, and $R^9$ are hydrogen;

$R^{12}$ is hydrogen, alkyl, hydroxy or aryl, wherein $R^{12}$ is optionally substituted with one or more, the same or different, $R^{20}$;

$R^{13}$, $R^{14}$, and $R^{15}$ are, individually and independently, hydrogen, alkyl, or halogen; and $R^{20}$ is alkyl, halogen, hydroxy, amino, or mercapto.

2. The compound of claim 1, wherein

Y is NH and $R^{12}$ is hydroxy.

3. The compound of claim 1, wherein
Y is NH and
$R^{12}$ is aryl optionally substituted with $R^{20}$.

4. The compound of claim 1 which is methyl (1R,2R)-1-(3,4-dichlorophenyl)-2-(((4-(hydroxycarbamoyl)benzyl)amino)methyl)cyclopropane-1-carboxylate or salt thereof.

5. The compound of claim 1 which is methyl (1R,2R)-2-(((4-((2-aminophenyl)carbamoyl)benzyl)amino)methyl)-1-(3,4-dichlorophenyl)cyclopropane-1-carboxylate or salt thereof.

6. The compound of claim 1 which is 4-(((((1R,2S)-2-(diethylcarbamoyl)-2-phenylcyclopropyl)methyl)amino)methyl)-N-hydroxybenzamide or salt thereof.

7. A composition comprising a compound of claim 1 in greater than 60% diastereomeric excess.

8. A pharmaceutical composition comprising a compound of claim 1 and a pharmaceutically acceptable excipient.

9. The compound of claim 3, wherein $R^{12}$ is phenyl optionally substituted with $R^{20}$.

10. The compound of claim 9, wherein $R^{12}$ is substituted with $R^{20}$.

11. The compound of claim 10, wherein $R^{20}$ is amino.

12. The compound of claim 3, wherein $R^{12}$ is 2-amino-phen-1-yl.

* * * * *